(12) United States Patent
Bromberg et al.

(10) Patent No.: US 10,918,356 B2
(45) Date of Patent: Feb. 16, 2021

(54) ULTRASOUND TRANSDUCERS HAVING ELECTRICAL TRACES ON ACOUSTIC BACKING STRUCTURES AND METHODS OF MAKING THE SAME

(71) Applicant: General Electric Company, Schenectady, NY (US)

(72) Inventors: Vadim Bromberg, Schenectady, NY (US); Lowell Scott Smith, Schenectady, NY (US); Douglas Glenn Wildes, Ballston Lake, NY (US); Kwok Pong Chan, Troy, NY (US); Reinhold Bruestle, Zipf (AT); Matthew Harvey Krohn, Lewistown, PA (US); Chester Frank Saj, Amsterdam, NY (US)

(73) Assignee: General Electric Company, Schenectady, NY (US)

( * ) Notice: Subject to any disclaimer, the term of this patent is extended or adjusted under 35 U.S.C. 154(b) by 797 days.

(21) Appl. No.: 15/358,160

(22) Filed: Nov. 22, 2016

(65) Prior Publication Data

US 2018/0140278 A1 May 24, 2018

(51) Int. Cl.
*A61B 8/00* (2006.01)
*G01S 15/89* (2006.01)
(Continued)

(52) U.S. Cl.
CPC ............ *A61B 8/4494* (2013.01); *A61B 8/461* (2013.01); *A61B 8/52* (2013.01); *B06B 1/0622* (2013.01);
(Continued)

(58) Field of Classification Search
CPC ...... A61B 8/4483; A61B 8/4494; A61B 8/461; A61B 8/52; A61B 8/00; B06B 1/0622;
(Continued)

(56) References Cited

U.S. PATENT DOCUMENTS

| 5,465,724 A | 11/1995 | Sliwa, Jr. et al. |
| 5,493,541 A | 2/1996 | Snyder |

(Continued)

FOREIGN PATENT DOCUMENTS

| JP | 08079895 A | * | 3/1996 |
| WO | 2007116362 A1 | | 10/2007 |

(Continued)

OTHER PUBLICATIONS

Translation of Sasazaki 1996.*
(Continued)

*Primary Examiner* — Carolyn A Pehlke

(57) ABSTRACT

An ultrasound transducer includes a transducer array having a plurality of transducer elements. The transducer array has a first side and a second side. Further, one or more ground electrodes are disposed on the first side of the transducer array, and one or more signal electrodes are disposed on the second side of the transducer array. Moreover, an acoustic backing structure is operatively coupled to the plurality of transducer elements of the transducer array. Also, a plurality of electrical traces is routed on a surface of the acoustic backing structure and operatively coupled to at least one of the one or more signal electrodes and one or more ground electrodes.

14 Claims, 13 Drawing Sheets

(51) Int. Cl.
*G01S 7/52* (2006.01)
*A61B 8/08* (2006.01)
*B06B 1/06* (2006.01)
*G10K 11/00* (2006.01)

(52) U.S. Cl.
CPC ........ *G01S 7/5208* (2013.01); *G01S 15/8915* (2013.01); *G10K 11/004* (2013.01)

(58) Field of Classification Search
CPC ....... B06B 1/64; B06B 1/0662; B06B 1/0685; B06B 1/0692; B06B 1/0696; G01S 7/5208; G01S 15/8915; G10K 11/004
See application file for complete search history.

(56) References Cited

U.S. PATENT DOCUMENTS

| | | | |
|---|---|---|---|
| 5,617,351 | A | 4/1997 | Bertin et al. |
| 5,709,209 | A * | 1/1998 | Friemel .................... A61B 8/00 600/447 |
| 5,923,115 | A | 7/1999 | Mohr, III et al. |
| 5,938,612 | A * | 8/1999 | Kline-Schoder ........ B06B 1/064 310/334 |
| 6,266,857 | B1 | 7/2001 | Corbett, III et al. |
| 6,383,141 | B1 * | 5/2002 | Itoi .......................... A61B 8/12 600/459 |
| 6,830,778 | B1 | 12/2004 | Schulz et al. |
| 7,015,795 | B2 | 3/2006 | Doudoumopolous |
| 7,199,305 | B2 | 4/2007 | Cruchon-Dupeyrat et al. |
| 7,277,770 | B2 | 10/2007 | Huang |
| 7,402,849 | B2 | 7/2008 | Liu et al. |
| 7,893,549 | B2 | 2/2011 | Bucchignano et al. |
| 7,935,565 | B2 | 5/2011 | Brown et al. |
| 7,947,612 | B2 | 5/2011 | Cain |
| 8,316,518 | B2 | 11/2012 | Lukacs et al. |
| 8,372,472 | B2 | 2/2013 | Hampden-Smith et al. |
| 8,604,671 | B2 | 12/2013 | Shikata |
| 8,668,848 | B2 | 3/2014 | Vanheusden et al. |
| 8,987,808 | B2 | 3/2015 | Cain et al. |
| 9,153,437 | B2 | 10/2015 | Rolandi et al. |
| 9,180,490 | B2 | 11/2015 | Tai |
| 9,180,491 | B2 | 11/2015 | Tsuzuki et al. |
| 9,247,926 | B2 | 2/2016 | Smith et al. |
| 2003/0085635 | A1 | 5/2003 | Davidsen |
| 2006/0173343 | A1 * | 8/2006 | Guo ........................ A61B 8/14 600/459 |
| 2006/0183335 | A1 | 8/2006 | Lowrey et al. |
| 2007/0104882 | A1 | 5/2007 | Kodas et al. |
| 2009/0178165 | A1 | 7/2009 | Shile |
| 2010/0277040 | A1 | 11/2010 | Klee et al. |
| 2012/0181902 | A1 | 7/2012 | Gelly et al. |
| 2013/0289593 | A1 | 10/2013 | Hall et al. |
| 2013/0310679 | A1 * | 11/2013 | Natarajan ............... A61B 8/445 600/411 |
| 2014/0268076 | A1 | 9/2014 | Huff et al. |
| 2014/0316269 | A1 | 10/2014 | Zhang et al. |
| 2015/0182194 | A1 | 7/2015 | Bruestle et al. |
| 2019/0029646 | A1 * | 1/2019 | Yamamoto ............... A61B 8/12 |

FOREIGN PATENT DOCUMENTS

| | | |
|---|---|---|
| WO | 2009158552 A1 | 12/2009 |
| WO | 2015068868 A1 | 5/2015 |

OTHER PUBLICATIONS

Learning About Electronics ("Why does a Circuit Always Have to Have Ground?", http://www.learningaboutelectronics.com/Articles/Why-does-a-circuit-always-have-to-have-ground, May 8, 2012).*

P Singh et al., "Additive manufacturing of PZT-5H piezoceramic for ultrasound transducers", Ultrasonics Symposium (IUS), 2011 IEEE International, pp. 1111-1114, Oct. 18-21, 2011, Orlando, FL.

K R Chapagain et al., "Grooved Backing Structure for CMUTs", IEEE Transactions on Ultrasonics, Ferroelectrics, and Frequency Control, vol. 60 Issue: 11, pp. 2440-2452, Nov. 2013.

PCT Invitation to Pay Addition Fees issued in connection with corresponding PCT Application No. PCT/US2017/060294 dated Jan. 30, 2018.

PCT Search Report and Written Opinion issued in connection with corresponding PCT Application No. PCT/US2017/060294 dated Mar. 22, 2018.

* cited by examiner

ULTRASOUND TRANSDUCERS HAVING ELECTRICAL TRACES ON ACOUSTIC BACKING STRUCTURES AND METHODS OF MAKING THE SAME

BACKGROUND

Embodiments of the present specification relate to ultrasound transducers and methods for routing electrical traces on acoustic backing structures of the ultrasound transducers.

Ultrasound is a widely used modality in medical imaging. Ultrasound imaging is typically used in cardiology, obstetrics, gynecology, abdominal imaging, and the like. An ultrasound transducer of an ultrasound system generally includes a transducer array, an acoustic backing structure, and electrical traces. The transducer array includes a plurality of transducer elements. Further, the ultrasound transducer includes matching layers that are attached to the front of the transducer to enhance transfer of energy between the transducer elements and a tissue of interest in a patient. The acoustic backing structure of the ultrasound transducer is used to restrict sound waves present at the back of the transducer from interfering with sound waves that are present at the front of the transducer. Electrical connections between the transducer elements and driving circuitry for the ultrasound transducer are typically routed via a flex circuit. In particular, the transducer elements are electrically coupled to electrical traces present on the flex circuit, and the electrical traces in turn are electrically coupled to the driving circuitry to provide electrical signal transmission, for example.

Usually, the flex circuit is used to route the electrical connections between the transducer elements and the driving circuitry of the ultrasound transducer. In particular, a signal flex and ground flex are used to provide a connection from each transducer element to the driving circuitry of the ultrasound system. At one end, the signal flex and ground flex are connected to signal and ground electrode(s) that are coupled to the transducer elements, and at the other end, the signal flex is usually connected to a group of wires in a cable bundle that is connected to the driving circuitry of the ultrasound system via a standard connector. Disadvantageously, with the increase in the number of transducer elements, this cable bundle tends to become stiff due to larger number of connections corresponding to the increased number of the transducer elements. Additionally, current flex circuit used in manufacturing of ultrasound transducers typically has two or more layers of conducting patterns, which need to be electrically isolated for proper functioning of the ultrasound transducer.

BRIEF DESCRIPTION

In one embodiment, an ultrasound transducer includes a transducer array having a plurality of transducer elements. The transducer array has a first side and a second side. Further, one or more ground electrodes are disposed on the first side of the transducer array, and one or more signal electrodes are disposed on the second side of the transducer array. Moreover, an acoustic backing structure is operatively coupled to the plurality of transducer elements of the transducer array. Also, a plurality of electrical traces is routed on a surface of the acoustic backing structure and operatively coupled to at least one of the one or more signal electrodes and one or more ground electrodes.

In another embodiment, an ultrasound system includes an acquisition subsystem having an ultrasound transducer probe that houses an ultrasound transducer. The acquisition subsystem is configured to acquire image data. The ultrasound transducer includes a transducer array having a plurality of transducer elements. The transducer array has a first side and a second side. Further, one or more ground electrodes are disposed on the first side of the transducer array, and one or more signal electrodes are disposed on the second side of the transducer array. Moreover, an acoustic backing structure is operatively coupled to the plurality of transducer elements of the transducer array. Also, a plurality of electrical traces is routed on a surface of the acoustic backing structure and operatively coupled to at least one of the one or more signal electrodes, and one or more ground electrodes. The ultrasound system also includes a processing subsystem configured to process the acquired image data, and a display device configured to display the acquired image data, the processed image data, or both.

In yet another embodiment, a method for routing a plurality of electrical traces on a target surface of the acoustic backing structure is provided. The method includes providing a first electrically conducting material having first electrically conducting particles. Further, the method includes additively fabricating a first layer of the first electrically conducting material on at least a portion of the target surface of the acoustic backing structure by moving a nozzle head in one or more directions along the acoustic backing structure.

DRAWINGS

These and other features and aspects of embodiments of the invention will become better understood when the following detailed description is read with reference to the accompanying drawings in which like characters represent like parts throughout the drawings, wherein.

Figure 8:
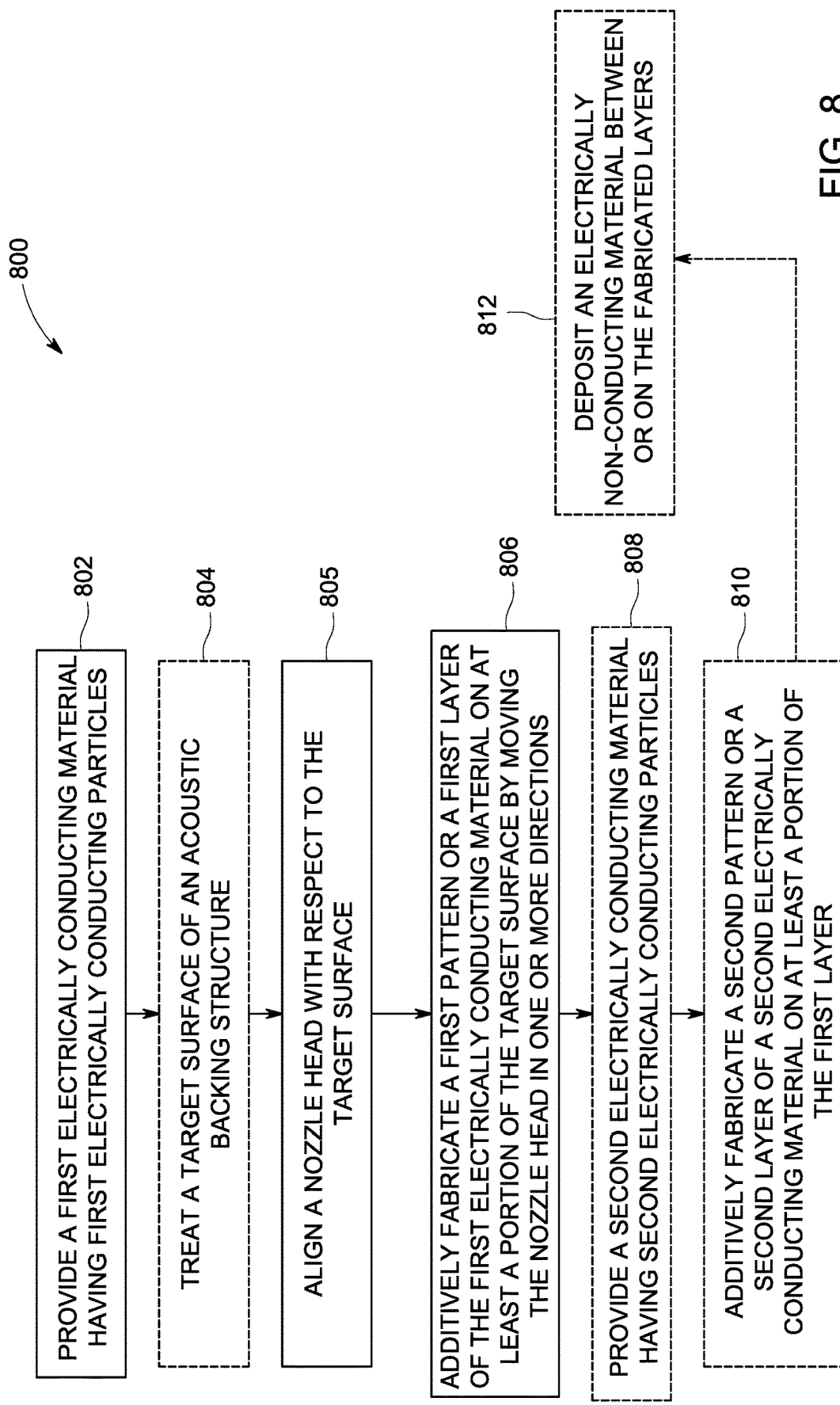
Figure 9:
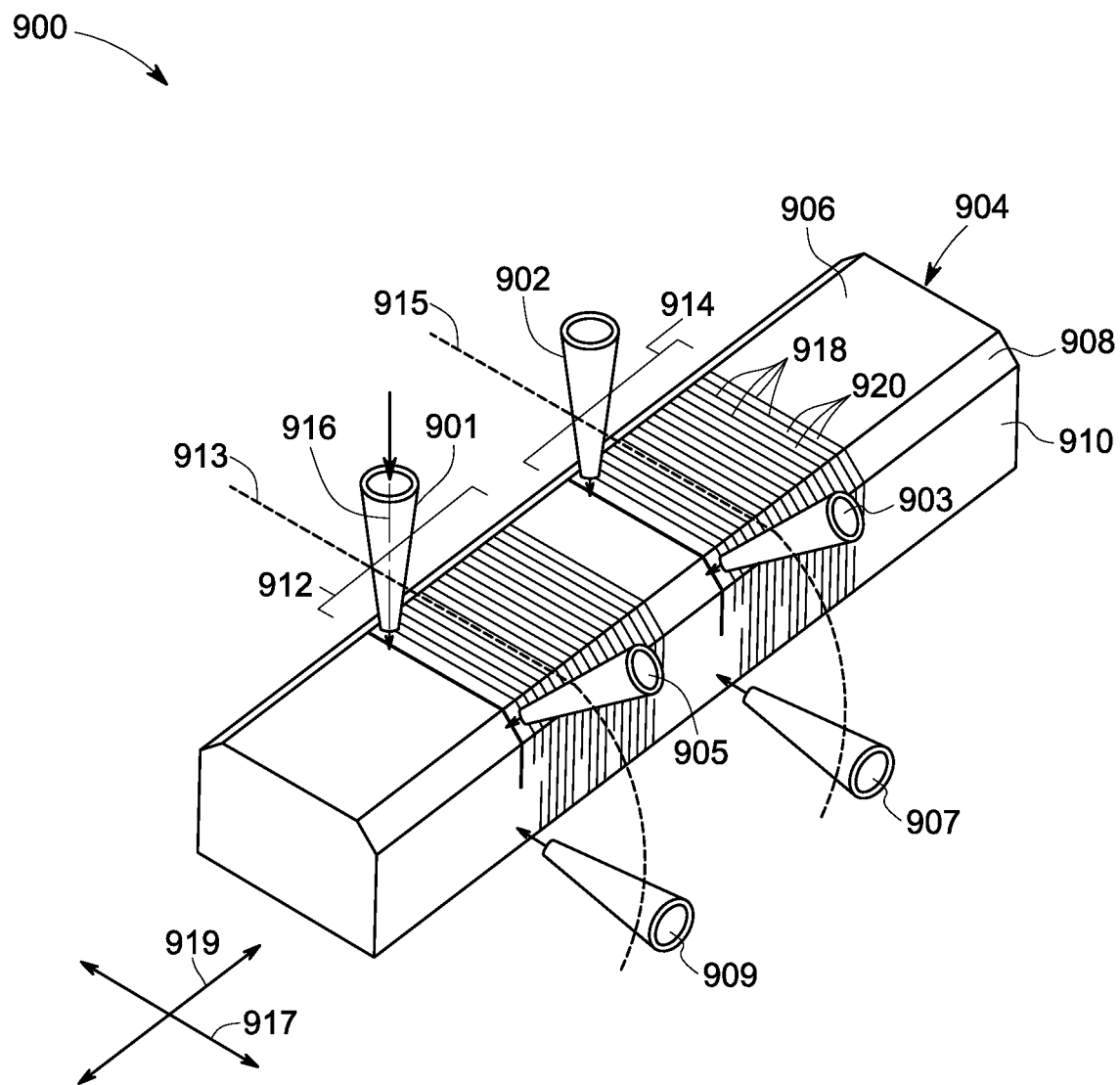

FIG. 8 is an exemplary flow chart of a method for routing a plurality of electrical traces on an acoustic backing structure, in accordance with aspects of the present specification; and FIG. 9 is a schematic representation of a configuration for routing a plurality of electrical traces on a surface of an acoustic backing structure using a nozzle head that is configured to translate in one or more directions, rotate in one or more directions, or both, in accordance with aspects of the present specification.

DETAILED DESCRIPTION

Embodiments of an ultrasound transducer or an ultrasound transducer probe formed using an additive fabricating method for routing a plurality of electrical traces on an acoustic backing structure are presented. In certain embodiments, processes for additive fabricating to route electrical traces on a surface of the acoustic backing structure of an ultrasound transducer are provided. In particular, electrical traces are provided on the surface of the acoustic backing structure to enable electrical coupling between a plurality of transducer elements of a transducer array and driving circuitry of an ultrasound system employing the ultrasound transducer. The plurality of electrical traces includes a plurality of signal traces and a plurality of ground traces. The electrical traces are routed on the acoustic backing structure such that there is electrical isolation between the individual electrical traces, and between the signal traces and one or more electrodes of the ultrasound transducer.

It may be noted that the terms "transducer" and "ultrasound transducer" are used interchangeably throughout the present specification.

In some embodiments, the systems and methods disclosed herein use one or more electrically conducting materials or inks to form the plurality of electrical traces. The electrically conducting materials are deposited as fine electrical traces along predefined paths on the surface of the acoustic backing structure. The electrical traces may include one or more layers. Further, in some embodiments, the methods disclosed herein may also include depositing one or more electrically insulating materials or inks using additive fabrication techniques. For example, the electrically insulating materials may be deposited between two or more electrical traces of the plurality of electrical traces, or at least on a portion of selected electrical traces, or both, to provide desirable electrical isolation to the electrical traces. Additionally, or alternatively, the electrically insulating materials may be deposited between the electrical traces and the electrodes of the ultrasound transducer. By way of example, the electrically insulating materials may be deposited between the signal traces and ground electrodes. In one example, a direct write technology may be used to deposit the electrically conducting inks and/or electrically insulating inks.

As will be appreciated, generally, in an ultrasound transducer, a complex and expensive interposer flex circuit is disposed on the acoustic backing structure to provide electrical connections between the transducer elements and the driving circuitry of the ultrasound transducer. In certain embodiments, the ultrasound transducer of the present specification includes an acoustic backing structure that includes electrical traces that are deposited directly on a surface of the acoustic backing structure using additive fabricating to provide electrical connections between the transducer elements and driving circuitry of the transducer. Consecutively, the ultrasound transducer of the present specification does not require a complex flex circuit disposed on the acoustic backing structure. Advantageously, due to direct deposition of the electrical traces on the surface of the acoustic backing structure, the only flex circuit employed in the ultrasound transducer of the present specification may be relatively simple and low cost flex circuit, such as an interposer circuitry that is configured to facilitate electrical connections between selected electrical traces and electrodes. Advantageously, by circumventing the use of the complex and expensive flex circuit via use of a surface of a component (acoustic backing structure) of the ultrasound transducer to route the electrical traces, cost and complexity in the design of the ultrasound transducer or ultrasound transducer probe is reduced considerably.

Although, the exemplary embodiments illustrated hereinafter are described in the context of an acoustic backing structure for use in a medical imaging system such as an ultrasound imaging system, it will be appreciated that use of such an acoustic backing structure in an ultrasound imaging system in other applications such as equipment diagnostics and inspections, baggage inspections, security applications are also envisaged.

Figure 1:
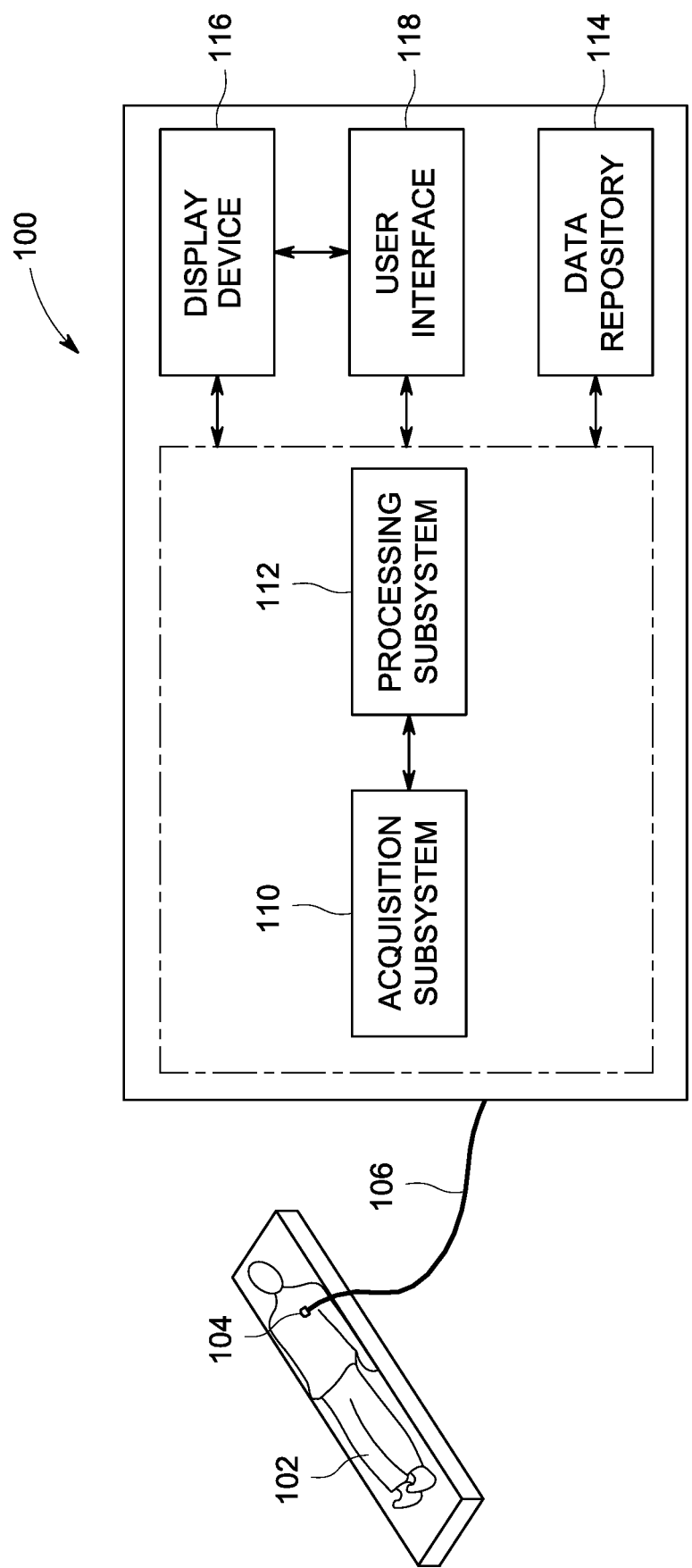
FIG. 1 is a diagrammatical illustration of an exemplary ultrasound system, in accordance with aspects of the present specification.

FIG. 1 illustrates an exemplary medical imaging system, such as an ultrasound system 100, for use in imaging, in accordance with aspects of the present specification. The system 100 is configured to facilitate acquisition of image data from an object of interest such as a patient 102 via an ultrasound transducer probe 104, for example. However, in certain other embodiments, the object of interest may include luggage, a sample, other equipment, and the like. The probe 104 may be configured to acquire image data representative of a region of interest in the patient 102. In some embodiments, the probe 104 may be configured to facilitate interventional procedures. Accordingly, in these embodiments, the probe 104 may include an invasive probe. In some other embodiments, the probe 104 may include a non-invasive probe. In the present non-limiting example of FIG. 1, the object of interest includes a patient 102 and the ultrasound transducer probe 104 is a non-invasive probe. Non-limiting examples of the probe 104 may include a transthoracic probe, endoscopes, laparoscopes, catheter-based probes, surgical probes, transrectal probes, transvaginal probes, intracavity probes, probes adapted for interventional procedures, other external probes, or combinations thereof. The probe 104 houses an ultrasound transducer (not shown in FIG. 1). The ultrasound transducer includes a transducer array (not shown in FIG. 1) having a plurality of transducer elements (not shown in FIG. 1).

In certain embodiments, the probe 104 may include an imaging catheter-based probe. Further, an imaging orientation of the imaging catheter may include a forward viewing catheter, a side viewing catheter, or an oblique viewing catheter. However, a combination of forward viewing, side viewing and oblique viewing catheters may also be employed as the imaging catheter.

Reference numeral 106 represents an electrical cable that connects the probe to other components of the ultrasound system 100. In particular, the cable 106 provides electrical connection between the ultrasound transducer and driving circuitry (not shown in FIG. 1) of the system 100. Specifically, the cable 106 provides the electrical connection between the plurality of transducer elements of the transducer array of the ultrasound transducer and the driving circuitry of the system 100. The plurality of transducer elements is configured to generate and transmit acoustic energy to the patient 102. Further, the plurality of transducer elements is also configured to receive backscattered acoustic signals from the patient 102 to create and display an image. In addition to the transducer array, the ultrasound transducer also includes one or more acoustic matching layers disposed on a first side of the transducer array, an interconnect circuit or interposer circuit disposed on a second side of the transducer array, a lens, an acoustic backing structure, and a plurality of electrical traces routed on a surface of the acoustic backing structure. The interposer circuit is configured to operatively couple the transducer array to the driving circuit of the system 100 via the acoustic backing structure. The acoustic backing structure may be present in the form of a highly attenuative backing layer for attenuating acoustic waves. Additionally, the lens may be disposed on an acoustic matching layer and configured to provide an interface between the patient 102 and the matching layer. In certain embodiments, the lens may be configured to direct and focus acoustic acoustic energy transmitted by the transducer elements to the patient 102. Alternatively, the lens may include a nonfocusing layer. The acoustic matching layers may be configured to facilitate matching of an impedance differential that may exist between the high impedance transducer elements and the low impedance patient 102.

In embodiments of the present specification, the electrical traces are routed on the acoustic backing structure in a conformal manner using additive fabricating. As used herein, the term "conformal manner," "conformally deposited," or "conformally routed" refers to deposition of electrical traces using additive fabrication on a surface of the acoustic backing structure such that the electrical traces follow one or more contours, turns, curvature, edges, and surface profiles of the surface of the acoustic backing structure on which the electrical traces are disposed.

The system 100 may be in operative association with the probe 104 and configured to facilitate acquisition and/or processing of image data. To that end, the system 100 may include an acquisition subsystem 110 and a processing subsystem 112. The image data acquired and/or processed by the system 100 may be employed to aid, for example, a clinician, in identifying disease states, assessing need for treatment, determining suitable treatment options, tracking the progression of the disease, and/or monitoring the effect of treatment on the disease states.

Although not illustrated in FIG. 1, the acquisition subsystem 110 also includes transmit/receive switching circuitry, a transmitter, a receiver, and a beamformer. In certain embodiments, the plurality of transducer elements is arranged in a spaced relationship to form a transducer array, such as, but not limited to, a one-dimensional or a two-dimensional transducer array. In certain embodiments, the transducer elements may be fabricated employing piezoelectric or micro-machined electro-mechanical (MEMS) materials, such as but not limited to, lead zirconate titanate (PZT), lead magnesium niobate titanate (PMNT), composite PZT, or micro-machined silicon.

When ultrasound waves are transmitted into the patient 102, the ultrasound waves are backscattered off the tissue and blood within the patient 102. The ultrasound transducer receives the backscattered waves at different times, depending on the distance into the tissue the waves return from and the angle with respect to the surface of the transducer assembly at which the waves return. The transducer elements convert the ultrasound energy from the backscattered waves into electrical signals. In one embodiment, the transducer assembly may be a two-way transducer.

In certain embodiments, the processing subsystem 112 may be coupled to a storage system, such as the data repository 114, where the data repository 114 is configured to store the acquired image data. Although not illustrated, the processing subsystem 112 may include a control processor, a demodulator, an imaging mode processor, a scan converter, and a display processor. In one example, the display processor may be coupled to a display monitor/device 116 for displaying images. User interface 118 may be used to interact with the control processor and the display monitor/device 116. The control processor may also be coupled to a remote connectivity subsystem including a web server and a remote connectivity interface. The processing subsystem 112 may be further coupled to data repository, such as the data repository 114, and configured to receive ultrasound image data. The data repository interacts with an imaging workstation.

Further, the system 100 may be configured to display the acquired image data using the display device 116 and the user interface area 118. In accordance with aspects of the present specification, the display device 116 may be configured to display the image generated by the system 100 based on the image data acquired via the imaging probe 104. Additionally, the display device 116 may be configured to aid the user in visualizing the generated image. In certain embodiments, such as in a touch screen, the display device 116 and the user interface 118 may overlap.

Aforementioned components may be dedicated hardware elements such as circuit boards with digital signal processors or may be software running on a general-purpose computer or processor such as a commercial, off-the-shelf personal computer (PC). The various components may be combined or separated according to various embodiments of the present specification. Thus, as will be appreciated, the present ultrasound imaging system is provided by way of example, and the present systems and methods are in no way limited by the specific system configuration. Further, although the exemplary embodiments illustrated hereinafter are described in the context of a medical imaging system, such as an ultrasound imaging system, other imaging systems and applications such as industrial imaging systems and non-destructive evaluation and inspection systems, such as pipeline inspection systems, liquid reactor inspection systems are also contemplated. For example, the exemplary embodiments illustrated and described hereinafter may find application in industrial borescopes that are employed for thickness monitoring, interface monitoring, or crack detection. Additionally, the exemplary embodiments illustrated and described hereinafter may find application in multi-modality imaging systems that employ ultrasound imaging in conjunction with other imaging modalities, position-tracking systems or other sensor systems.

Moreover, in certain embodiments, a transducer assembly is disposed in a transducer probe, such as the probe 104 of FIG. 1. Advantageously, the transducer assembly or the ultrasound transducer probe of the present specification does not include a complex flex circuit that is typically used to provide electrical communication between the transducer elements of the transducer array and the driving circuitry of the transducer probe 104. In certain embodiments, electrical traces operatively coupling the transducer elements or the transducer array to the driving circuitry of the ultrasound transducer are directly deposited on an outer surface of the acoustic backing structure.

In certain embodiments, the plurality of electrical traces includes signal and ground traces, which are routed on the acoustic backing structure to electrically couple the ultrasound transducer to the driving circuitry or signal cabling of the ultrasound system. Further, the ground traces may be coupled to the ground electrode to provide ground connection. In some embodiments, use of a chamfer or radius of the acoustic backing structure, thickness control of the signal traces, thickness control of an insulating layer disposed on the signal traces, or combinations thereof may be used to electrically isolate the signal traces on the acoustic backing structure from ground contacts or ground electrodes of the transducer elements of the ultrasound transducer. By way of example, a portion of the acoustic backing structure may be chamfered to provide physical separation between the signal traces on the acoustic backing structure and ground electrodes on the transducer array. Additionally, an electrically insulating layer may be disposed on at least a portion of the signal traces to provide electrical insulation between the signal traces and the ground electrodes. In some embodiments, electrically insulating material may be deposited between the electrical traces to electrically isolate the electrical traces from one another. In some of these embodiments, the electrically insulating material may be disposed between the electrical traces using additive fabrication. Additionally, in some embodiments, after assembly of the ultrasound transducer to provide desirable coupling between the electrical traces and signal and ground electrodes, electrically insulating layer may be disposed or deposited on portions of the signal and/or ground traces to prevent undesirable electrical contact of these electrical traces with other components or circuitry of the ultrasound transducer.

Advantageously, the systems and methods described in this application may be employed in the manufacturing processes of existing ultrasound probes with minimal or no modification required in the components of the existing ultrasound transducer or the ultrasound probe. For example, to convert an existing ultrasound transducer to an ultrasound transducer of the present specification, the complex flex circuit may be decoupled from the acoustic backing structure, removed from the probe, and replaced with electrical traces that are routed on the surface of the acoustic backing structure in a conformal manner using additive fabrication. Advantageously, utilization of component surface area, that is, surface area of the acoustic backing structure, for forming electrical traces for circuit metallization frees up space inside the ultrasound probe.

In certain embodiments, routing of the electrical traces on the acoustic backing structure may include one or more additive fabricating techniques. Accordingly, in some of these embodiments, materials are deposited, usually layer upon layer, to make three-dimensional objects. Various exemplary methods of additive fabricating usable with the present specification may include processes, such as, but not limited to, direct write, electron beam deposition, laser deposition, stereo-lithography, three-dimensional (3D) printing, and combinations thereof.

In some embodiments, the method includes direct write processes to print electrically conducting and insulating inks as fine traces in one or more layers along predefined paths on the surface of the acoustic backing structure. Advantageously, direct routing of the traces on the acoustic backing structure serves to replace the use of costly and complex flex circuit, which is traditionally used to provide electrical connection between the transducer elements of the transducer array and the driving circuitry. It may be noted that the electrically conducting material for the electrical traces may include liquid materials filled with a high volume concentration of metal particles.

Advantageously, the electrical traces may be formed on planar, curved, angular, or part planar and part curved surfaces of the acoustic backing structure. In certain embodiments, routing the electrical traces includes routing the signal traces as well as ground traces, while providing electrical insulation between the signal and ground traces. Further, while forming these electrical traces, electrical insulation is provided between signal traces and the ground electrodes.

Figure 2A:
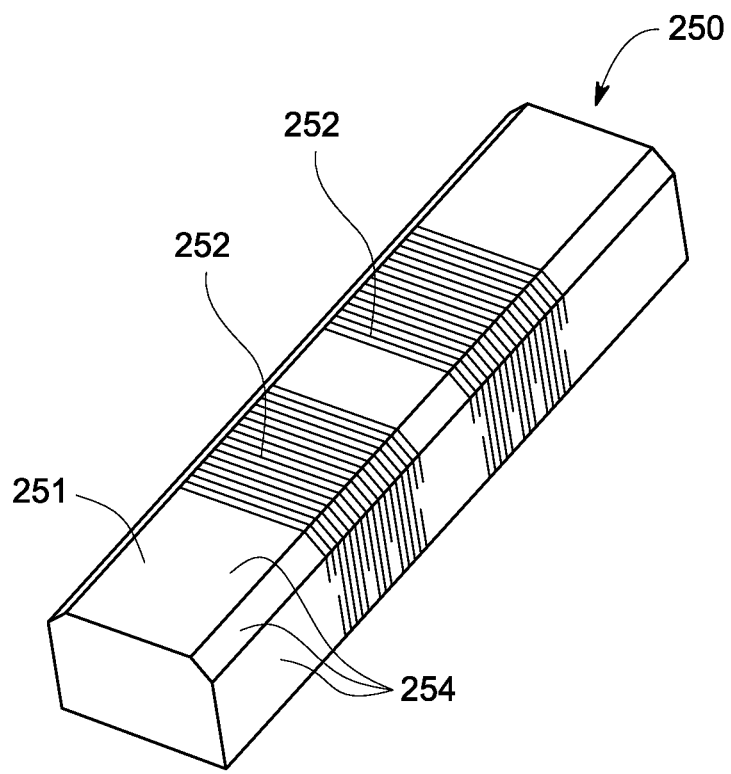
FIGS. 2A-2B are schematic representations of an acoustic backing structure having planar surfaces, where a plurality of electrical traces is routed on at least a portion of the planar surfaces of the acoustic backing structure, in accordance with aspects of the present specification.
Figure 2B:
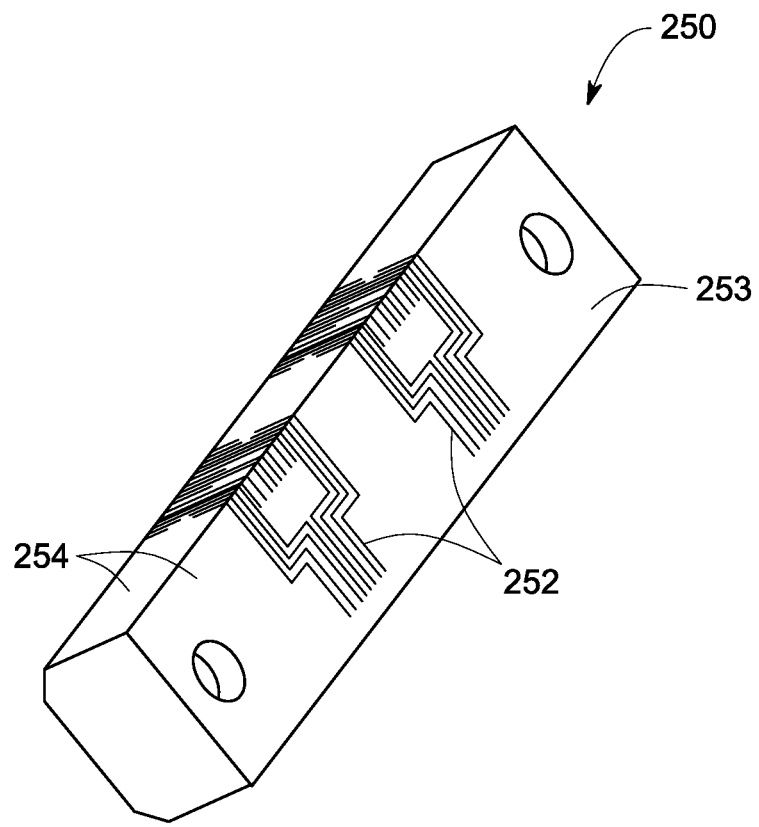

FIGS. 2A-2B illustrate an example acoustic backing structure 250 having a combination of planar surfaces 254. FIG. 2A represents a first side 251 of the acoustic backing structure 250 and FIG. 2B represents a second side 253, disposed opposite the first side 251, of the acoustic backing structure 250. A plurality of electrical traces 252 is disposed directly on portions of the planar surfaces 254 of the acoustic backing structure 250. The plurality of electrical traces 252 includes both signal and ground traces. In some embodiments, the acoustic backing structure 250 may be an acoustic backing structure of an existing ultrasound transducer. In some of these embodiments, the complex flex circuit coupled to the acoustic backing structure may be decoupled from the acoustic backing structure 250 and electrical traces may be routed on the acoustic backing structure 250. Further, the electrical traces may be suitably connected to signal or ground electrodes of the ultrasound transducer. The acoustic backing structure 250 may have a planar surface, an undulated surface, a curved surface, a slanted surface, an angular surface, joints, bends, or combinations thereof. The electrical traces 252 may be conformally deposited on the surface 254 using additive fabrication. In certain embodiments, the electrical traces 252 are conformally deposited using movement of a nozzle head of an additive fabrication set-up during additive fabrication process.

Figure 3:
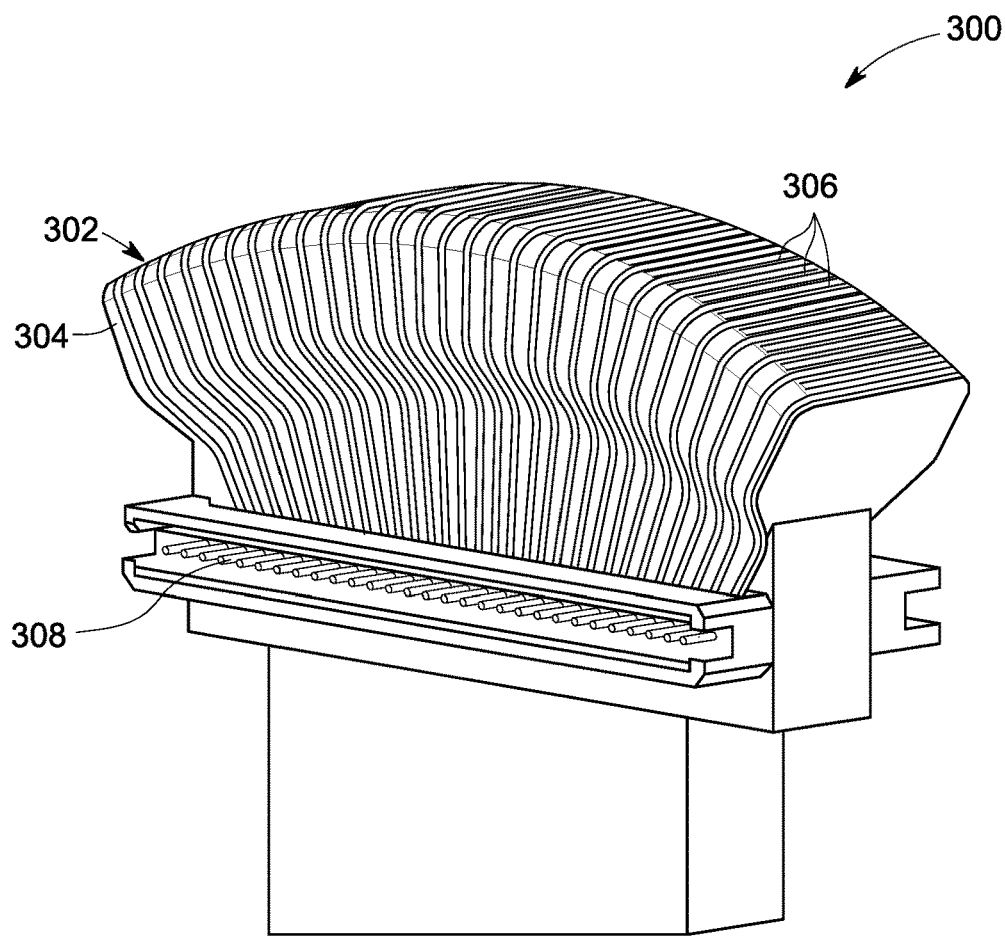
FIG. 3 is a schematic representation of an acoustic backing structure having a curved surface, where a plurality of electrical traces is disposed on at least a portion of the curved surface of the acoustic backing structure, in accordance with aspects of the present specification.

FIG. 3 illustrates an exemplary acoustic backing structure 300 having a curved surface 302 and planar surfaces 304. A plurality of electrical traces 306 is disposed directly on the surfaces 302 and 304 of the acoustic backing structure 300. Further, the electrical traces 306 are conformally routed on the curved and planar surfaces 302 and 304 using additive fabrication. On one side the electrical traces 306 are connected to signal or ground electrodes (not shown in FIG. 3), on the other side, the electrical traces 306 may be connected to driving circuitry via a cable (not shown in FIG. 3), where the cable may be coupled to the electrical traces 306 via a port 308. The electrical traces 306 include signal traces, ground traces, or both.

FIGS. 4A-7D represent alternative embodiments for routing a plurality of electrical traces and providing electrical insulation between select electrical traces (e.g. signal traces) and ground electrodes of the ultrasound transducer. Non-limiting examples of ultrasound transducers having electrical traces routed on acoustic backing structures are illustrated in FIGS. 4A-7D. Various combinations of illustrated examples 4A-7D are envisioned with the purview of this application.

Figure 4A:
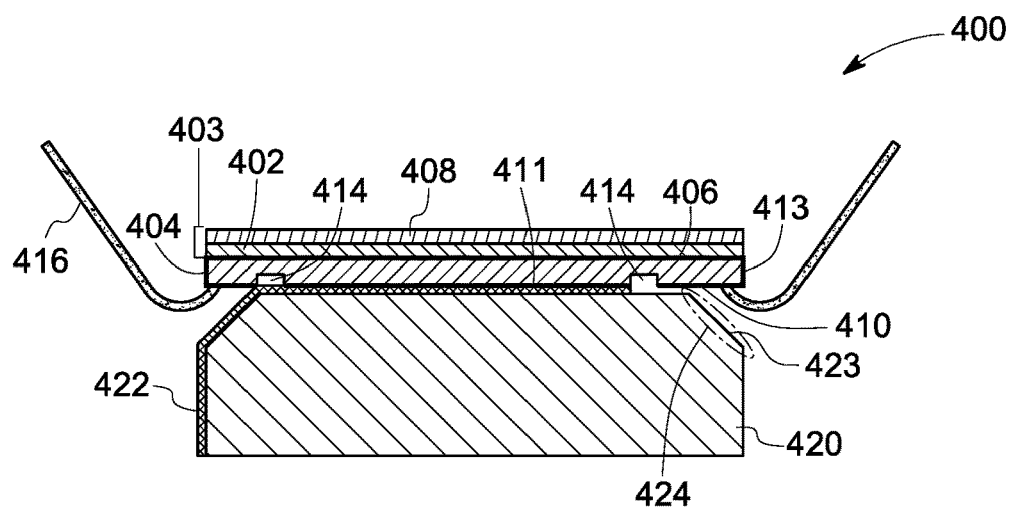
FIGS. 4A-7D are schematic representations of various embodiments for routing a plurality of electrical traces on an acoustic backing structure while providing electrical insulation between the plurality of electrical traces and one or more ground electrodes, in accordance with aspects of the present specification.
Figure 4B:
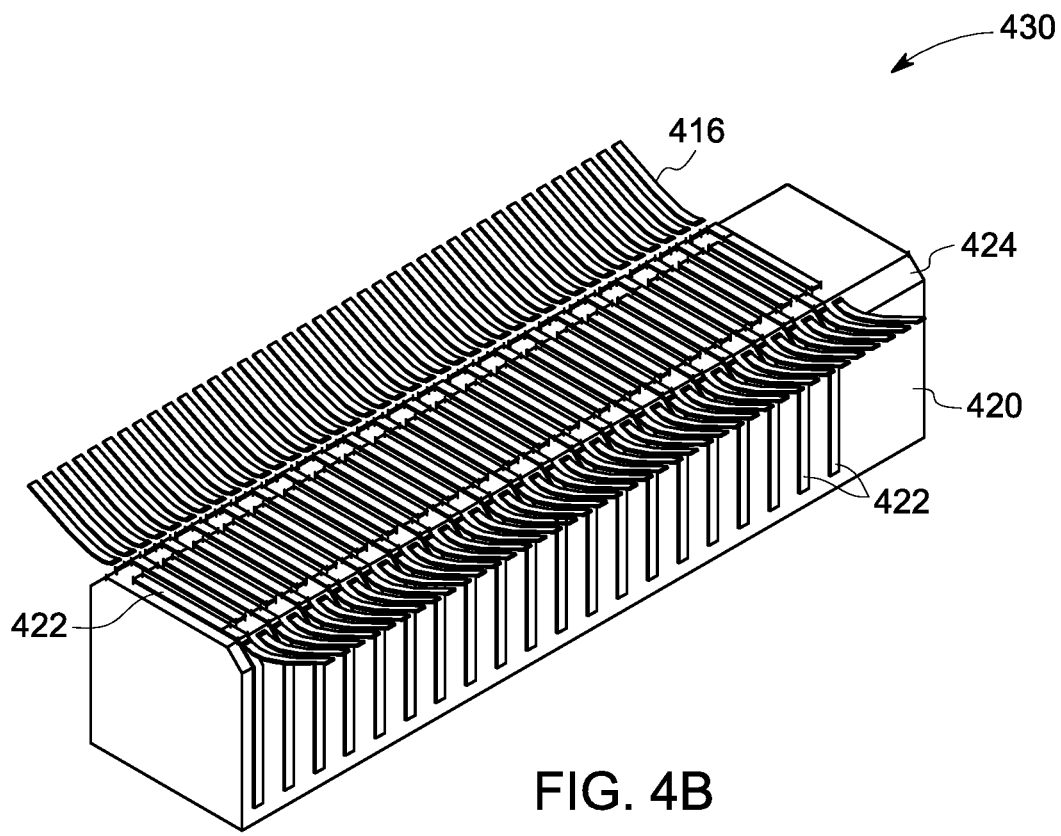
Figure 4C:
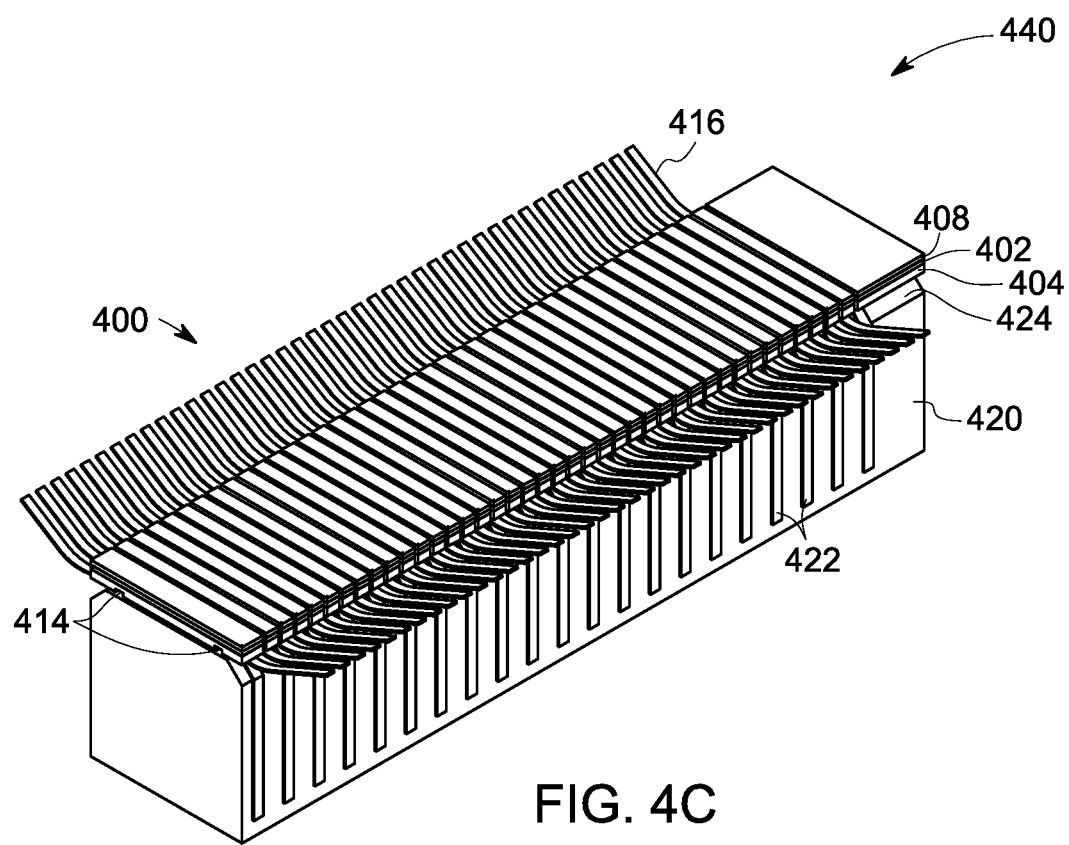

Turning now to FIGS. 4A-4C, FIG. 4A illustrates a cross-sectional view of an ultrasound transducer 400 having a transducer array 404 and optionally, a plurality of acoustic matching layers 403. The transducer array 404 may be made of a piezoelectric material with its surfaces metalized for use as electrodes. FIG. 4B represents a perspective view 430 of a portion of the ultrasound transducer 400 of FIG. 4A. Further, FIG. 4C represents a perspective view 440 of the ultrasound transducer 400 of FIG. 4A. The transducer array 404 has a first side 406 and a second side. The second side is divided by "isolation cuts" 414 into signal electrodes 411 (disposed between the isolation cuts 414) and ground electrodes 413. In one example, the transducer array 404 may include a piezoelectric (PZT) array; or binary or ternary piezoelectrics $(1-x)Pb(Mg_{1/3}Nb_{2/3})O_3$-$xPbTiO_3$ (PMNT) crystals. An acoustic matching layer 402 of a plurality of acoustic matching layers 403 is disposed on the first side 406 of the transducer array 404. Further, another acoustic matching layer 408 of the plurality of acoustic matching layers 403 is disposed on the acoustic matching layer 402. Further, in the illustrated embodiment, the transducer array 404 includes ground conductors 416 coupled to the ground electrodes 413. Additionally, the ultrasound transducer 400 includes an acoustic backing structure 420 having signal traces 422 and ground traces (not shown in FIGS. 4A-4C) that are routed on a surface 423 of the acoustic backing structure 420. The signal electrodes of the transducer array 404 are configured to be coupled to the signal traces 422 to transmit and receive ultrasound signals. Moreover, the ground electrodes 413 are configured to be coupled to the ground traces to provide ground connection to a plurality of transducer elements (not shown in FIGS. 4A-4C) of the transducer array 404. The transducer array 404 includes a grooves or passages, referred to as "isolation cuts" 414. Each isolation cut 414 is configured to electrically isolate the signal electrodes disposed on one side of the isolation cut 414 from the ground electrodes 413 disposed on the other side of the isolation cut 414. In a non-limiting example, the ground conductors 416 may be coupled to the transducer array 404 using solder.

Additionally, although not illustrated, optionally, an interconnect layer, also referred to as "interposer circuit," such as a simple flex circuit, may be disposed on the second side 410 of the transducer array 404. In particular, the interposer circuit may be disposed between the second side 410 of the transducer array 404 and the surface 423 of the acoustic backing structure 420 to provide electrical coupling between the transducer elements In certain embodiments, the acoustic backing structure 420 may be suitably shaped to provide electrical isolation between the ground conductors 416 of the transducer array 404 and the signal traces 422 routed on the acoustic backing structure 420. In the illustrated example, a portion 424 of the acoustic backing structure 420 is provided with a slope, chamfered, or cut, such that the signal traces 422 routed on the acoustic backing structure 420 are not in contact with the ground conductors 416 of the transducer array 404. Although not illustrated, in another embodiment, grooves may be provided in the acoustic backing structure 420, for example on the surface 423 of the acoustic backing structure 420, to accommodate portions of the ground conductors 416 such that the ground conductors 416 are disposed within these grooves and hence are physically separated and electrically isolated from the signal traces 422 of the acoustic backing structure. Alternatively, or additionally, the signal traces 422 may be disposed in grooves present on the second side 410 of the transducer array 404 to provide electrical isolation between the signal traces 422 and the ground conductors 416.

Figure 5A:
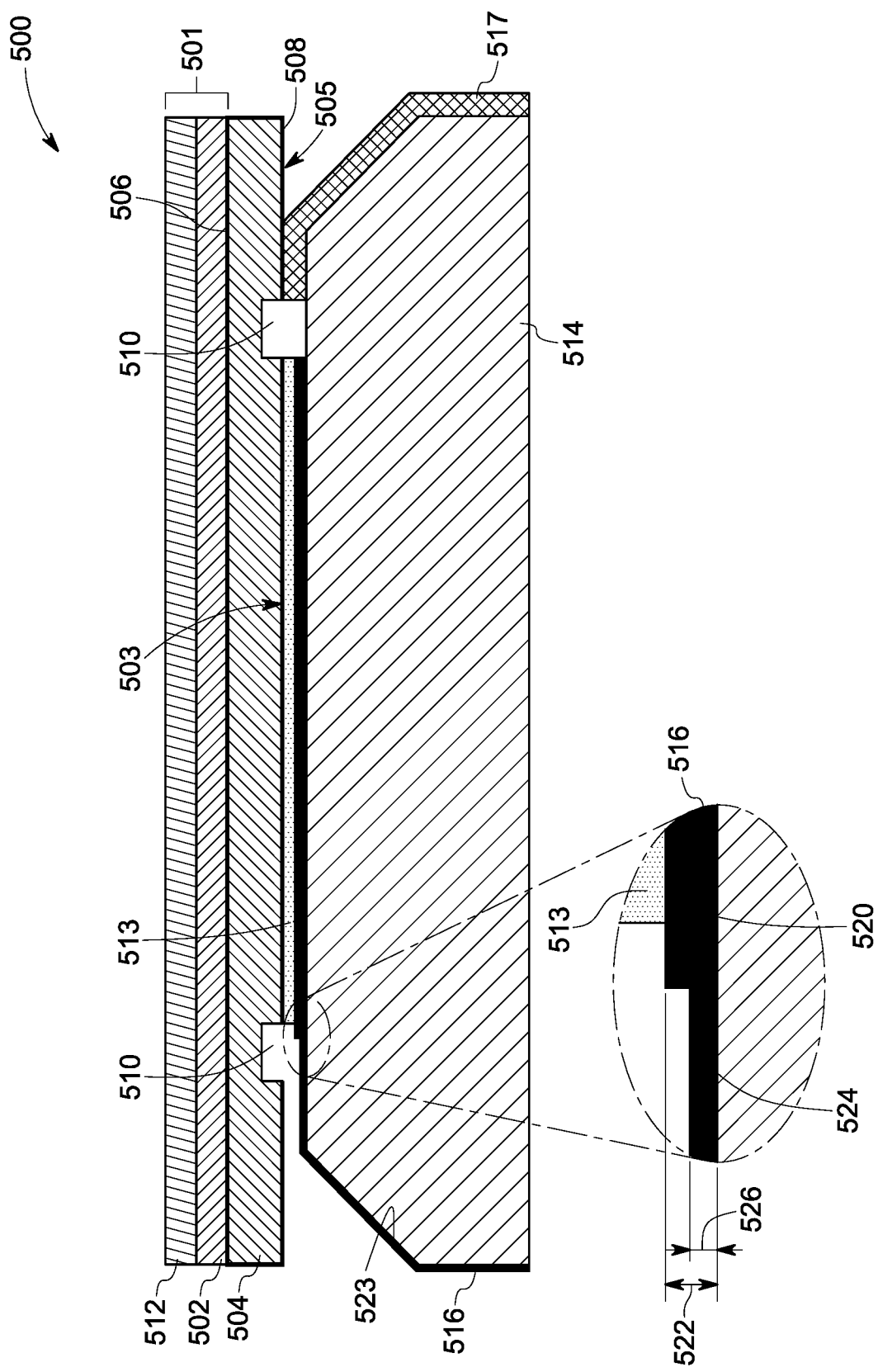
Figure 5B:
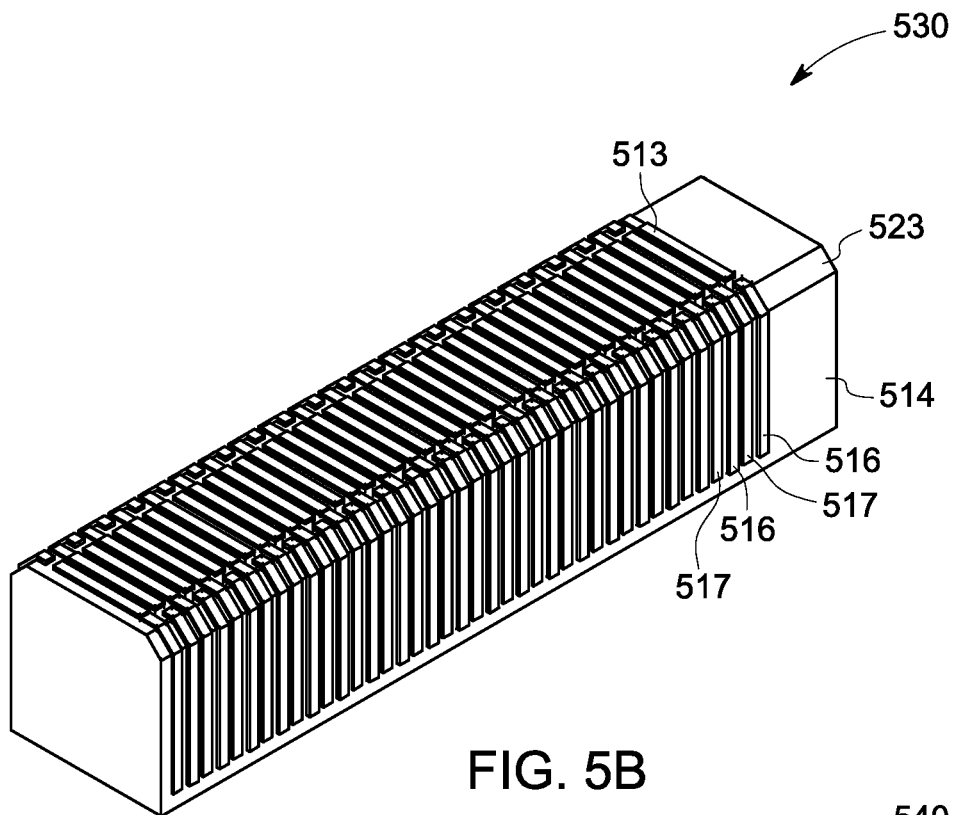
Figure 5C:
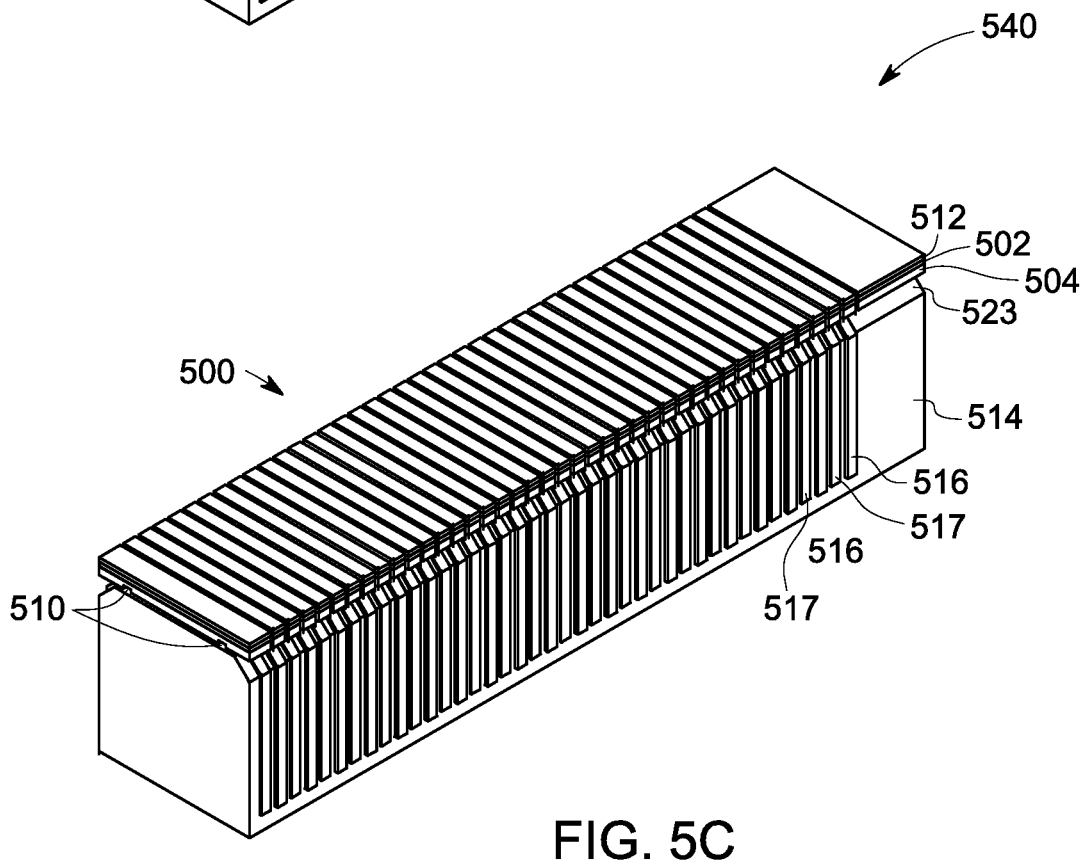

Referring to FIGS. 5A-5C, FIG. 5A illustrates a cross-sectional view of an ultrasound transducer 500 having a transducer array 504 and optionally, a plurality of acoustic matching layers 501. FIG. 5B represents a perspective view 530 of a portion of the ultrasound transducer 500 of FIG. 5A. Further, FIG. 5C represents a perspective view 540 of the ultrasound transducer 500 of FIG. 5A.

The transducer array 504 includes a first side 506 and a second side 508. An acoustic matching layer 502 of the plurality of acoustic matching layers 501 is disposed on the first side 506 of the transducer array 504. Further, another acoustic matching layer 512 of the plurality of acoustic matching layers 501 is disposed on the acoustic matching layer 502. Isolation cuts 510 are provided across a plurality of transducer elements of the transducer array 504, thereby separating signal electrodes 503 from ground electrodes 505. The signal electrodes 503 are disposed on the second side 508 of the transducer array 504 between the isolation cuts 510. Further, the ground electrodes 505 are disposed on the first side 506 as well as on a portion of the second side 508 of the transducer array 504. Optionally, in some embodiments, an interposer circuit 513 may also be disposed on the second side 508 of the transducer array 504. The ultrasound transducer 500 also includes an acoustic backing structure 514 disposed towards the second side 508 of the transducer array 504. The acoustic backing structure 514 includes signal traces 516 that are disposed directly on a surface of the acoustic backing structure 514. The signal traces 516 correspond to a plurality of transducer elements of the transducer array 504. Further, the acoustic backing structure 514 includes ground traces 517 disposed directly on the surface of the acoustic backing structure 514. The signal and ground traces 516 and 517 are configured to be coupled to signal and ground electrodes 503 and 505 of the transducer array 504. The signal traces 516 may have variable thickness to prevent undesirable electrical contact between the signal traces 516 present on the acoustic backing structure 514 and ground electrodes 505 of the transducer array 504. Varying thickness of the signal traces 516 may be particularly useful in embodiments where the flex circuit 513 is not employed between the transducer array 504 and the acoustic backing structure 514. In the illustrated example, a first portion 520 of the signal traces 516 includes a first thickness 522, and a second portion 524 of the signal traces 516 includes a second thickness 526, where the first thickness 522 is greater than the second thickness 526 such that the signal traces 516 are physically separated and electrically isolated from the ground electrodes 505 of the transducer array 504. The first and second thickness values 522 and 526 may be in a range from about 1 micron to about 20 microns. In one example, the second thickness value 526 may be in a range from about 20% to about 80% of the first thickness 522.

Although, in the illustrated embodiments of FIGS. 5A-5C, electrical isolation is provided to the signal traces by varying the thicknesses of the electrical traces as well as shaping portions 523 of the acoustic backing structure 514, it may be noted that in alternative embodiments, variable thicknesses of the signal traces 516 may be selected such that electrical isolation is provided to the electrical traces without chamfering the portions 523 of the acoustic backing structure 514.

Figure 6A:
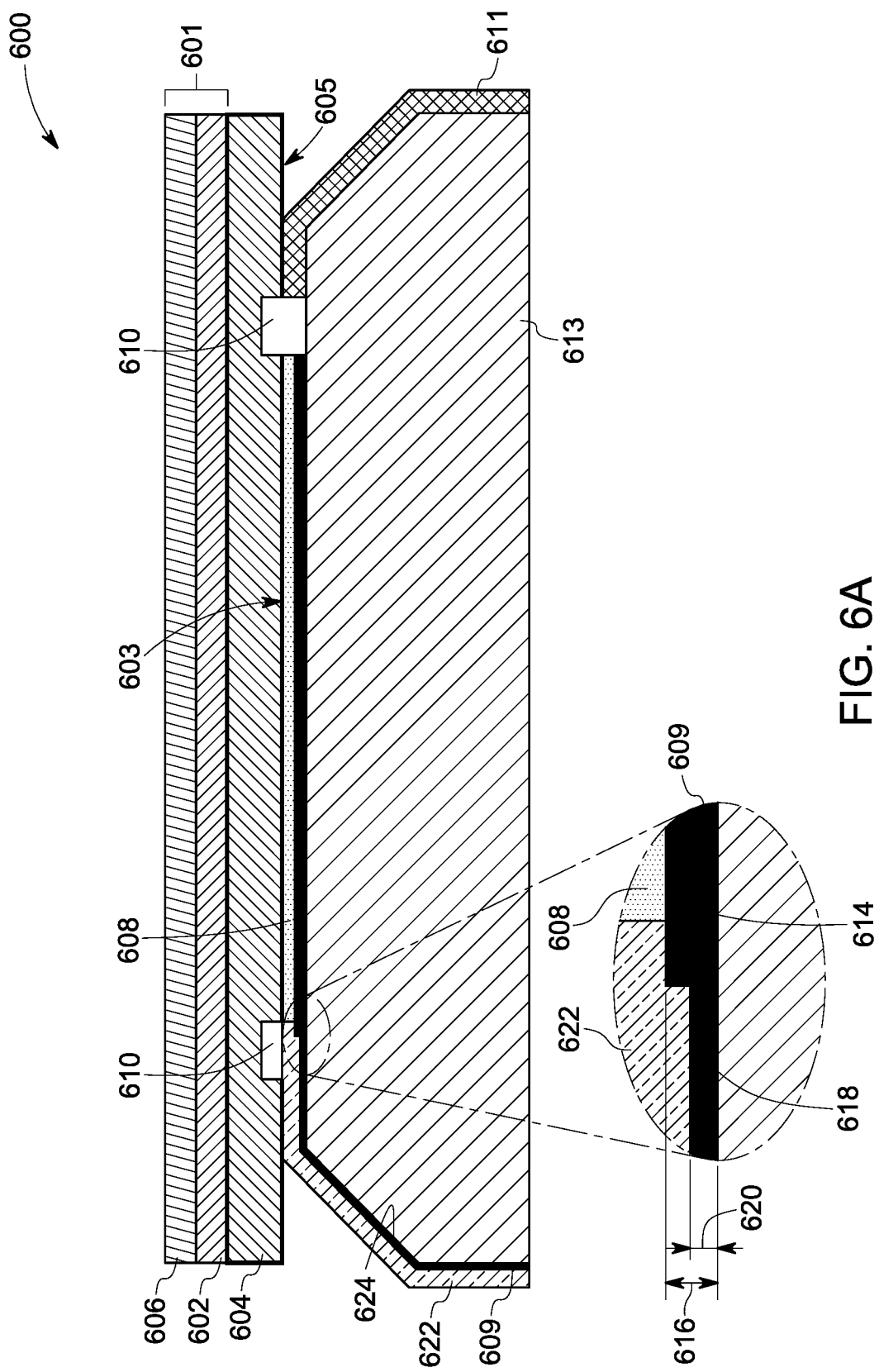
Figure 6B:
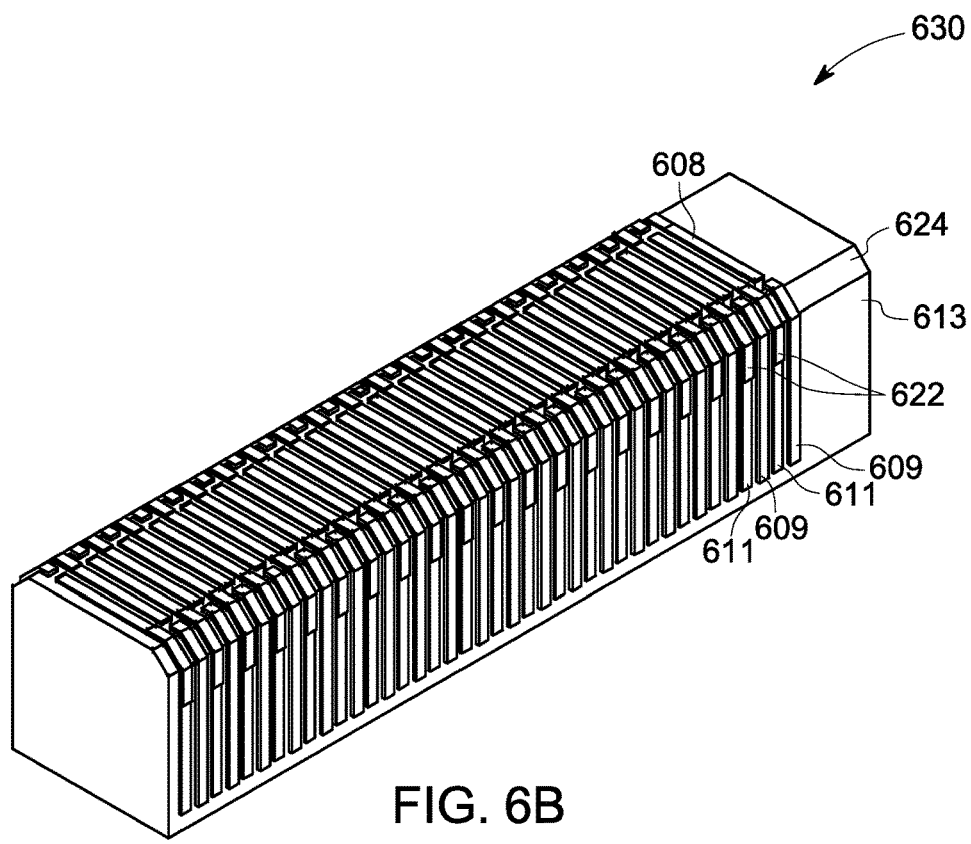
Figure 6C:
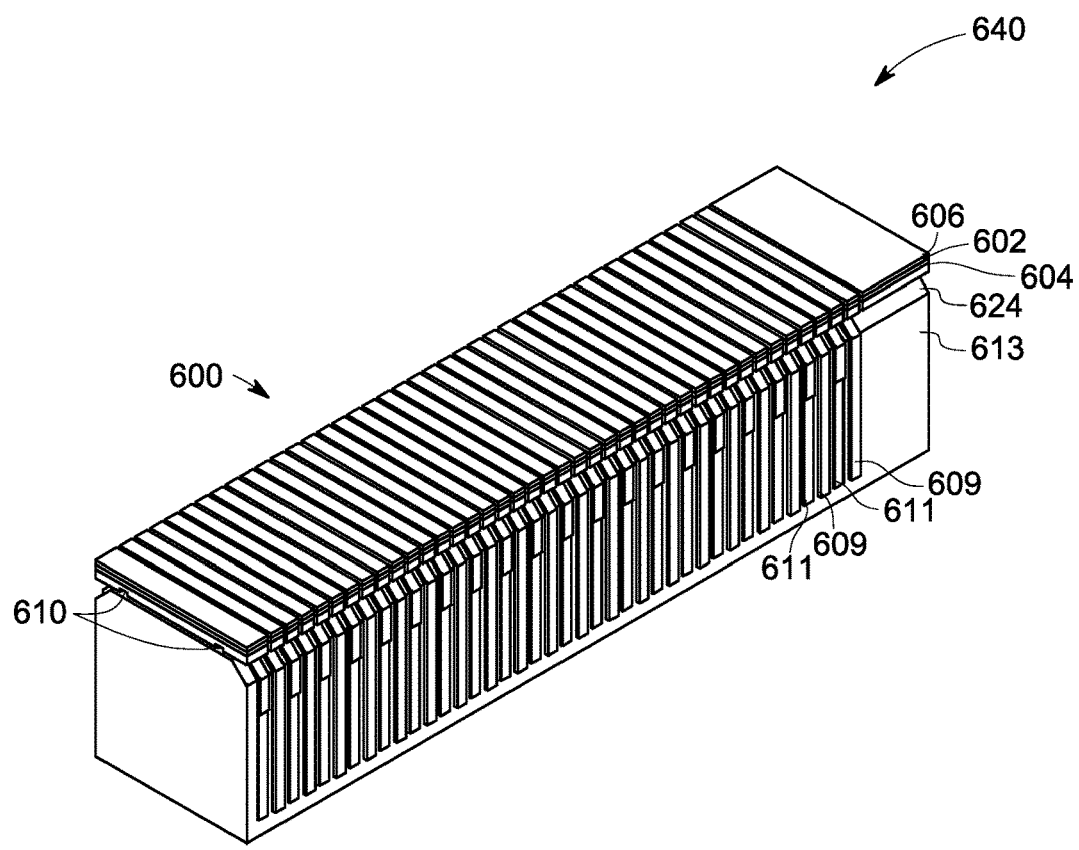

Turning now to FIGS. 6A-6C, FIG. 6A illustrates a cross-sectional view of an ultrasound transducer 600 having a transducer array 604 and a plurality of acoustic matching layers 601. FIG. 6B represents a perspective view 630 of a portion of the ultrasound transducer 600 of FIG. 6A. Further, FIG. 6C represents another perspective view 640 of a portion of the ultrasound transducer 600 of FIG. 6A. As illustrated in FIGS. 6A and 6C, an acoustic matching layer 602 is disposed on a first side of the transducer array 604 and another acoustic matching layer 606 is disposed on the acoustic matching layer 602. Isolation cuts 610 run across a plurality of transducer elements of the transducer array 604, thereby separating signal electrodes 603 (disposed between the isolation cuts 610) from ground electrodes 605. Further, optionally an interposer flex circuit 608 is disposed on a second side of the transducer array 604. The interposer flex circuit 608 may be used to support the signal and ground electrodes 603 and 605. In particular, the transducer arrays having curved outer surfaces may employ an interposer flex circuit, such as the circuit 608, to facilitate coupling of the transducer elements and the signal and ground electrodes 603 and 605.

An acoustic backing structure 613 is operatively coupled to the signal and ground electrodes 603 and 605 via signal and ground traces 609 and 611, respectively. The signal and ground traces 609 and 611 are disposed directly on the surface of the acoustic backing structure 613. Optionally, the signal traces 609 may have varying thickness values. By way of example, the signal traces 609 may include a first portion 614 having a first thickness 616, and a second portion 618 having a second thickness 620, where the first thickness is greater than the second thickness such that the signal traces 609 are physically separated and electrically isolated from the ground electrodes 605 of the ultrasound transducer 600. The first and second thicknesses 616 and 620 may be selected from a range of about 1 micron to about 20 microns. In one example, the second thickness 620 may be in a range from about 20% to about 80% of the first thickness 616. Alternatively, or in addition to varying the thickness of the signal traces 609, an insulating layer 622 may be disposed on at least a portion of the signal traces 609 to provide electrical insulation between the ground electrodes 605 of the transducer array 604 and the signal traces 609 routed on the acoustic backing structure 613.

Although not illustrated, in one embodiment, the signal traces 609 may have a uniform thickness throughout the length of the signal traces 609, and the insulating layer 622 may be disposed on selective portions of the signal traces or between signal traces 609 to provide electrical insulation between the signal traces 609 and the ground electrodes 605. Further, the thicknesses of selective portions of the signal traces 609, thicknesses of the insulating layer 622, or both may be selected such that electrical insulation between the signal traces 609 and the ground electrodes is provided without the need to chamfer portions 624 of the acoustic backing structure 613.

Figure 7A:
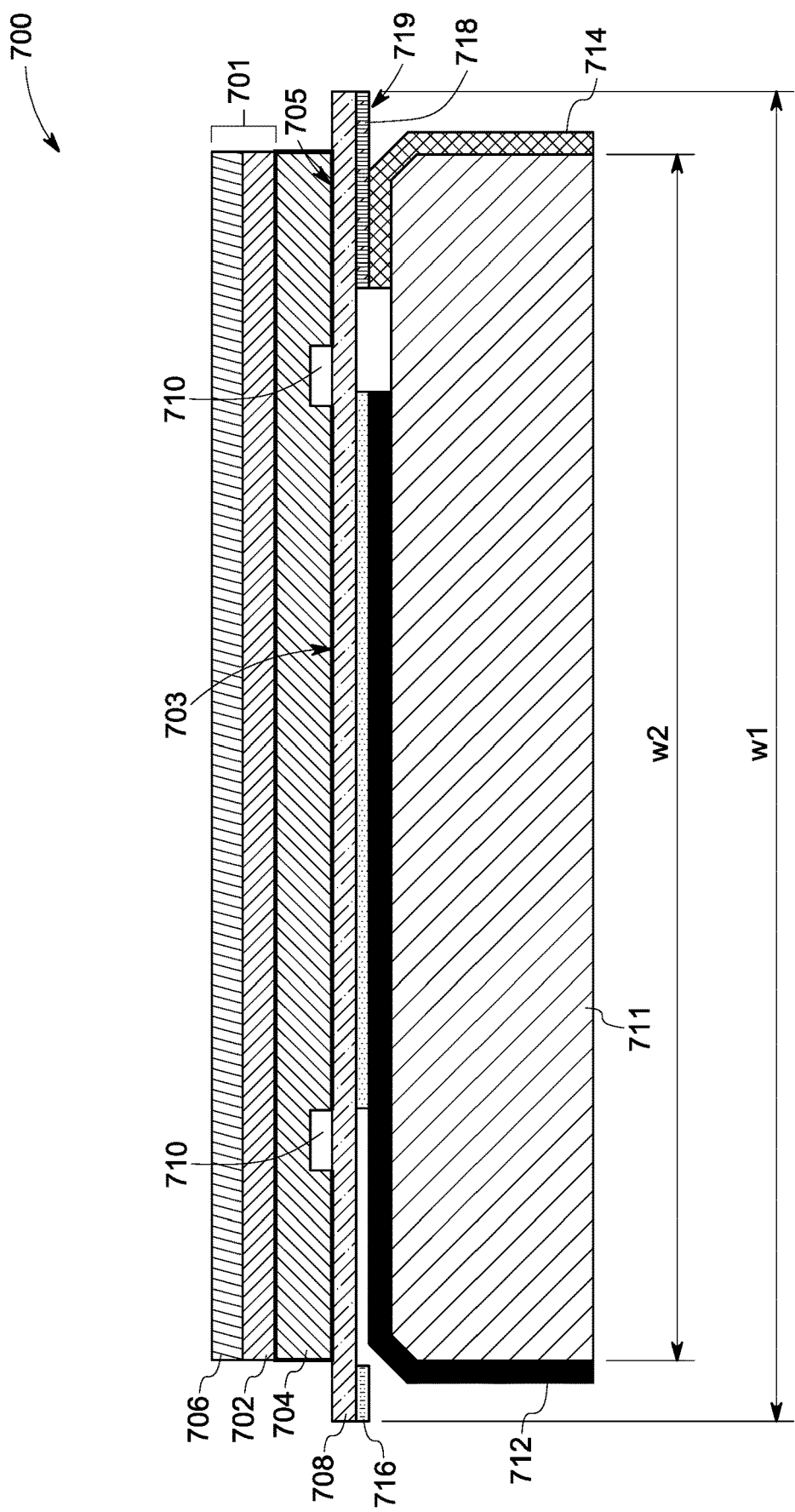
Figure 7B:
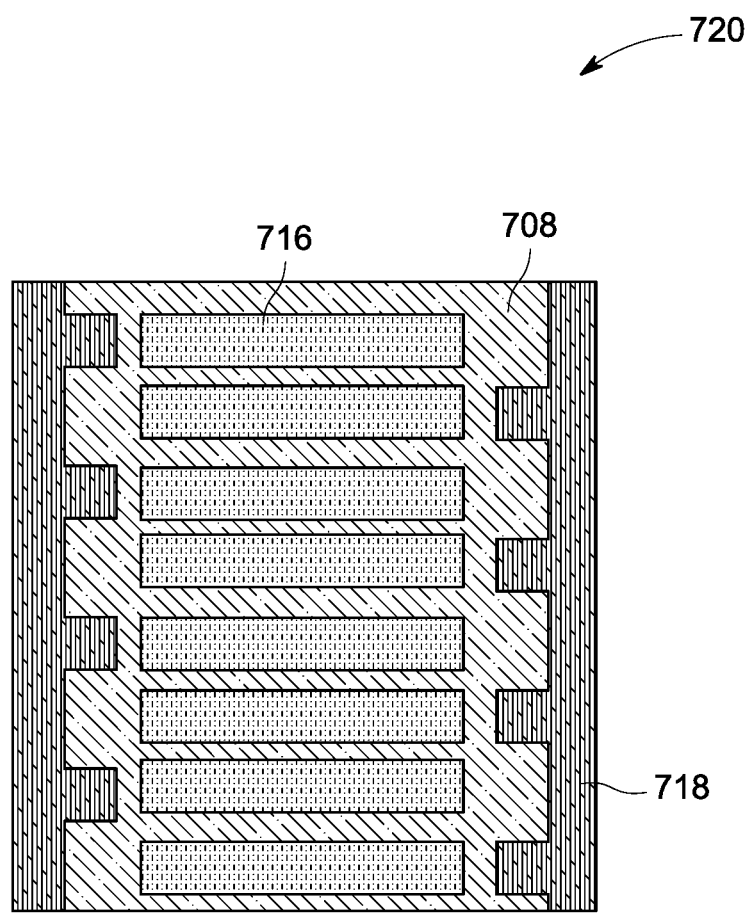
Figure 7C:
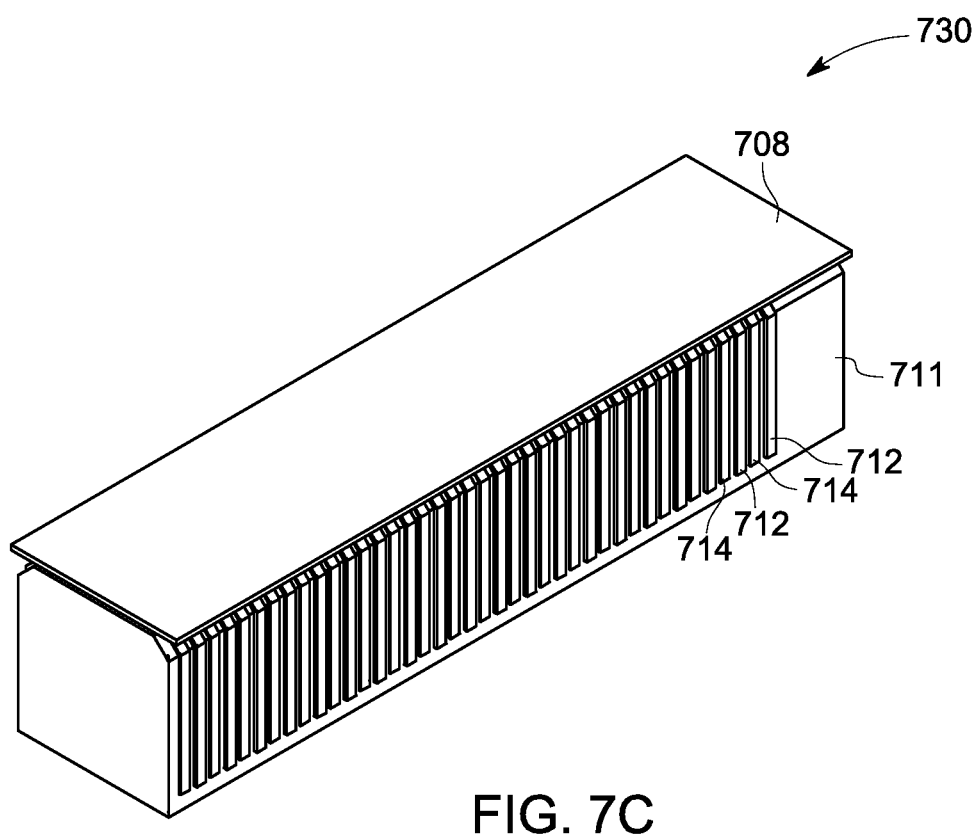
Figure 7D:
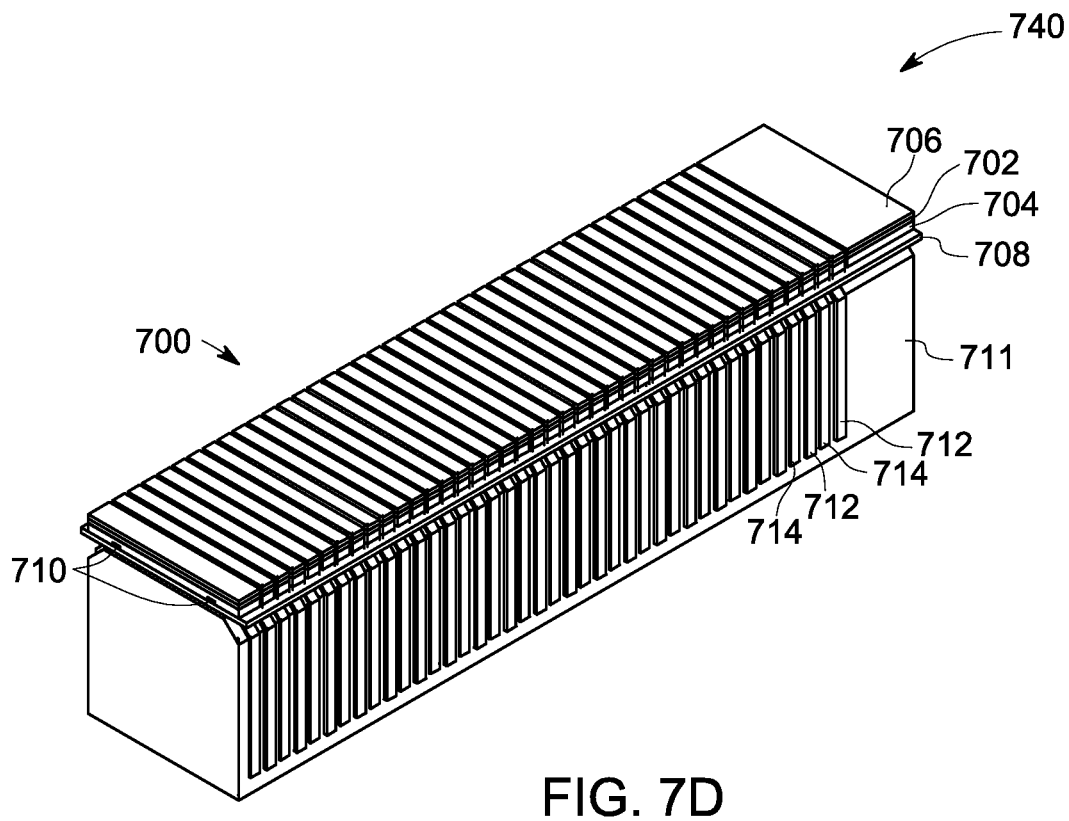

Referring to FIGS. 7A-7D, FIG. 7A illustrates a cross-sectional view of an ultrasound transducer 700 having a transducer array 704 and a plurality of acoustic matching layers 701. FIG. 7B illustrates a top view 720 of interdigitated electrodes operatively coupled to the transducer array 704. FIG. 7C represents a perspective view 730 of a portion of the ultrasound transducer 700 of FIG. 7A. Further, FIG. 7D represents a perspective view 740 of another embodiment of the ultrasound transducer 700 of FIG. 7A. FIGS. 7A-7D illustrate yet another embodiment for routing electrical traces on an acoustic backing structure in an ultrasound transducer 700. In the illustrated embodiment, an acoustic matching layer 702 of the plurality of acoustic matching layers 701 is disposed on the first side of the transducer array 704, another acoustic matching layer 706 is disposed on the acoustic matching layer 702. Further, optionally, an interposer flex circuit 708 disposed on the second side of the transducer array 704. Isolation cuts 710 run across a plurality of transducer elements of the transducer array 704. The interposer flex circuit 708 is wider than an acoustic backing structure 711. In the illustrated embodiment, the width of the interposer flex circuit 708 is represented as w1, and the width of the acoustic backing structure 711 is represented as w2.

Signal electrodes 716 and ground electrodes 718 are coupled to the interposer flex circuit 708 such that the ground electrodes 718 are not in physical contact with signal traces 712 that are routed on the acoustic backing structure 711. In particular, width and radius of curvature of the acoustic backing structure 711 is selected to facilitate isolation of the signal traces 712 and the ground electrodes 718.

The interposer flex circuit 708 may be used to support the signal and ground electrodes 716 and 718. In general, transducer arrays having curved exterior surfaces may employ an interposer flex circuit, such as the circuit 708, to facilitate coupling of the transducer elements and the signal and ground electrodes 716 and 718.

FIG. 7B represents the interposer flex circuit viewed from a direction represented by arrow 719 (see FIG. 7A). As illustrated, the ground electrodes 716 and the signal electrodes 718 form an interdigitated structure.

Although not illustrated the embodiments of FIGS. 4A-7D, electrically non-conducting materials/inks may be deposited between two or more electrical traces or on one or more electrical traces to provide electrical insulation or isolation to the electrical traces. Further, an adhesion promoter material or layer may be disposed on the surface of the acoustic backing structure before routing the electrical traces on the surface of the acoustic backing structure. Moreover, although embodiments illustrated herein depict and describe two acoustic matching layers, use of one or more than two acoustic matching layers is also envisioned within the purview of the present specification.

FIG. 8 is an example flow chart 800 of a method of additive fabrication of a plurality of electrical traces routed on a surface of the acoustic backing structure in accordance with embodiments of the present specification. The surface of the acoustic backing structure on which the plurality of electrical traces is routed may be referred to as a "surface" or a "target surface, accordingly, the terms "surface" and "target surface" may be used interchangeably in the description of FIGS. 8 and 9.

At block 802, the method commences by providing a first electrically conducting material or ink having first electrically conducting particles. The method may use more than one ink, such as a first electrically conducting ink, a second electrically conducting ink, and the like. These inks may be deposited layer upon layer using additive fabrication, and may or may not differ in chemical constitution from one another. In one embodiment, the step of providing an ink, such as the step 802 of providing the electrically conducting ink may include formulating the electrically conducting ink using one or more of electrically functional colloidal particles, a binder (e.g., polyurethane), a surfactant, one or more curing agents, a carrier solvent, or combinations thereof. Constituents of the ink formulation are selected such that the ink has suitable rheological properties (e.g., viscosity, surface tension, and the like) to facilitate consistent dispensing of the electrically conducting ink through a nozzle head of a dispenser.

To enhance adhesion of the electrical traces on the acoustic backing structure, one or more suitable adhesion-promoting binders may be mixed with the first electrically conducting ink. Optionally, at block 804, the surface of the acoustic backing structure may be treated prior to writing or depositing the electrical traces on the surface of the acoustic backing structure. In some examples, the surface of the acoustic backing structure may be exposed to plasma and/or laser, vapor, or subjected to print deposition methods to enhance adhesion of the ink for the electrical traces to the surface of the acoustic backing structure. In another example, the surface of the acoustic backing structure may be wetted with a suitable wetting agent. In one embodiment, controlled wetting of the target surface of the acoustic backing structure is performed to provide fine feature resolution for the electrical traces. In particular, depending on the solvent used for the ink and depending on the material of the target surface, low surface tension secondary solvents (e.g., alcohols). ionic, cationic, non-ionic surfactants, or one or more silanes, or combinations thereof, may be used as the wetting agent.

Due to fine dimensions of the electrical traces, it is desirable to have enhanced alignment between a nozzle head of the print device of the additive fabrication set-up, or a direct write device and a target area on the surface of the acoustic backing structure. At block 805, alignment may be provided between the target surface and a nozzle head of the additive fabrication device to deposit the electrically conducting material along predetermined paths on the surface of the acoustic backing structure. By way of example, imaging techniques may be used to locate fiducial reference features on the target surface. Prior knowledge of relative locations of the fiducials and the print nozzle head may be used for extrapolation of the locations of target areas on the surface of the acoustic backing structure where ink is to be deposited. In certain other embodiments, one or more three-dimensional scanning and registration techniques, such as, but not limited to, laser spot/line triangulation, structured light imaging, and/or touch probe scanning may be employed for enhancing the alignment between the nozzle head and the target area on the surface. The three-dimensional scanning and registration techniques may produce a three-dimensional point cloud data of the target surface. Analysis of this data such as image segmentation and/or pattern matching may be used to identify the locations of the target areas where ink is to be deposited.

In certain embodiments, a direct write process may be used for direct write dispense or jetting heads or nozzle heads that are movable in 3 or more directions to deposit an electrically conducting ink (such as a colloidal ink). The ink may be dispensed in the form of a highly-filled suspension or a slurry at various locations on a surface of an acoustic backing structure.

Further, in certain embodiments, the electrical traces may be additively fabricated on the target surface of the acoustic backing structure using layer by layer deposition. By way of example, at block 806, a first pattern or a first layer of the first electrically conducting material or ink is deposited on at least a portion of the target surface by moving and/or tilting the nozzle head in one or more directions. Further, the nozzle head may be moved along one or more axes to enable conformal deposition of the plurality of electrical traces. Typically, a width of an electrical trace may be between about 20 microns to about 200 microns across.

Upon deposition, the electrically conducting material may undergo a phase change and solidify due to solvent evaporation and/or light or thermally-induced polymerization of binder and curing agent, for example.

Thermal treatment of printed or deposited electrical traces may induce undesirable distortion in the target surface. To minimize transfer of heat to the target surface and subsequent distortion of the target surface, in some embodiments, a suitable thermal treatment may be provided to solidify and/or stabilize the ink. By way of example, spatially localized thermal treatment with an ultra violet (UV) source, an infrared (IR) source, and/or a laser source may be used for heat treating the deposited electrical traces.

Advantageously, by using techniques of the present specification, electrical traces having thickness in a range from about 1 micron to 10 microns may be deposited conformally on the target surface of the acoustic backing structure. Moreover, in instances where the electrical traces include two or more layers, different layers of the electrical layers may be made of same or different inks. In one example, at least one of the layers of the different layers may have an ink with a composition that is different than compositions of the inks of other layers.

In embodiments where the electrical traces include two or more layers, as illustrated at block 808, a second electrically conducting material having second electrically conducting particles is provided. The second electrically conducting material may include second electrically conducting particles. Further, the chemical compositions of the first and second electrically conducting materials may be same or different.

Optionally, at block 810, a second pattern or a second layer of the second electrically conducting material may be additively fabricated on at least a portion of the first layer. The second layer may be additively fabricated before or after solidification of the first layer. Further, the second layer may be deposited by moving the nozzle head in one or more directions along one or more axes.

Further, optionally, the second electrically conducting ink may be formulated using one or more electrically conducting particles. The second electrically conducting ink may be deposited on the first electrically conducting ink, and the process may be repeated based on a desirable number of layers in the electrical traces. Further, electrically non-conducting or insulating inks may be deposited, such as on portions of the signal traces, or between signal traces to provide electrical insulation between the signal traces and between the signal traces and the ground electrodes.

By repeating the process illustrated in blocks 802-810, a plurality of layers having either the same or different electrically conducting materials may be conformally deposited on the target surface of the acoustic backing structure.

Optionally, at block 812, an electrically non-conducting or insulating material is deposited between or on the deposited patterns or layers. By way of example, an electrically non-conducting or insulation material or ink may be deposited between the electrical traces or at least on a portion of the electrical traces. In one embodiment, an electrically insulating material may be deposited on at least a portion of the signal traces to provide electrical isolation between the signal traces and the ground electrodes of the transducer array. In the same or different embodiment, the electrically insulating material may be deposited between two or more electrical traces to provide electrical isolation between the electrical traces.

After deposition of the electrical traces, and optionally electrically conducting materials, an ultrasound transducer or transducer assembly may be formed by physically coupling the transducer array to the acoustic backing structure such that the electrical traces are suitably coupled to the electrodes of the transducer array.

Portions of signal traces that are not physically coupled to the electrodes may be coated with an electrically insulating material (for example, as shown in FIG. 6B) to prevent undesirable contact between the electrical traces and other components or circuitry of the ultrasound transducer. The electrically insulating layer may be deposited using coating techniques, such as, but not limited to, direct write technology, dip coating, spray coating, chemical vapor deposition, physical vapor deposition, or any other technique suitable for depositing material on relatively large areas.

By controlling the location and deposition rate of the deposited electrically conducting materials ink, a three-dimensional object may be built layer by layer. In certain embodiments, the method includes a direct write process to print electrically conducting and insulating inks as fine traces in one or more layers along predefined paths on the surface of the acoustic backing structure. This process serves to replace the use of a costly and complex flex circuit, which is traditionally used to provide electrical connection between the elements of the acoustic transducer array and the driving circuitry. It may be noted that the electrically conducting material for the electrical traces may include liquid materials filled with a high volume concentration of metal particles.

FIG. 9 illustrates a non-limiting example of a method step represented by blocks 805 and 806 of FIG. 8. In the illustrated arrangement 900, a nozzle head 901 of a printing or writing device (not shown in FIG. 9) is illustrated as being in different positions represented generally by reference numerals 902, 903, 905, 907 and 909. The nozzle head 901 is configured to be in different orientations by moving and/or tilting the nozzle head 901 to suit a profile of a surface of the acoustic backing structure 904. In the illustrated example, the nozzle head 901 is moved over sub-surfaces or surfaces that together form the surface of the acoustic backing structure 904. By way of example, in the illustrated embodiment, surfaces 906, 908 and 910 may be referred to as sub-surfaces of an acoustic backing structure. Although the surfaces 906, 908, and 910 are shown as planar surfaces, it may be noted that the arrangement 900 and methods of the present specification may also be used to route electrical traces on curved surfaces of the acoustic backing structure 904.

As illustrated, the nozzle head 901 at different locations 902, 903, 905, 907, and 909 is tilted by a determined angle to facilitate conformal deposition of the electrical traces on the surface of the acoustic backing structure 904. Lines 913 and 915 illustrate the path of motion of the nozzle head 901. In addition, the nozzle head 901 may also traverse in one or more directions, such as directions represented by arrows 917 and 919. Further, one or more nozzle heads may be used to deposit one or more layers of the electrical traces 918 in one or more locations, such as locations 912 and 914. In addition, same or different nozzle heads may be used to deposit electrically insulating materials, such as represented by reference numeral 920. In the illustrated embodiment, the electrically non-conducting or insulating material 920 may also be deposited in desirable regions, such as regions on or between the electrical traces 918 to provide electrical isolation between two or more electrical traces and electrical traces and ground electrodes.

Advantageously, various embodiments of the present technique allow routing of electrical and signal traces on an acoustic backing structure while providing electrical insulation between the ground electrodes and signal traces. It may be noted that combinations of various embodiments illustrated in FIGS. 4A-7D may be used to provide routing of the electrical traces in ultrasound transducers to obviate the need for a flex circuit for providing electrical connection between the transducer array and driving circuitry of the ultrasound transducer. By way of example, both chamfering a portion of the acoustic backing structure and insulating a portion of signal traces may be used to provide physical isolation and electrical insulation between the ground electrodes and signal traces. Advantageously, the electrical and signal traces of the present technique can be routed on existing acoustic backing structure. Further, the signal and ground traces may be employed in existing ultrasound transducers with minimal or no design alterations. In one embodiment, a probe size of the ultrasound probe may be reduced using the signal and ground traces of the present technique.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. An ultrasound transducer, comprising:
a transducer array having a first side and a second side and comprising a plurality of transducer elements;
a plurality of ground electrodes disposed on the first side of the transducer array;
a plurality of signal electrodes disposed on the second side of the transducer array;
an acoustic backing structure operatively coupled to the plurality of transducer elements of the transducer array, wherein the acoustic backing structure includes a complex curved surface comprising a curved surface and a plurality of planar surfaces, wherein the plurality of transducer elements of the transducer array are disposed on the curved surface;
a plurality of electrical traces routed on the complex curved surface of the acoustic backing structure, wherein the plurality of electrical traces comprises a plurality of signal traces and a plurality of ground traces, wherein one or more signal traces of the plurality of signal traces have a varying thickness, wherein each of the plurality of electrical traces is routed on the curved surface and at least one of the plurality of planar surface, wherein a first of the plurality of electrical traces is operatively connected to a first of the plurality of signal electrodes and a second of the plurality of electrical traces is operatively connected to a second of the plurality of the signal electrodes, wherein a third of the plurality of electrical traces is operatively connected to a first of the plurality of ground electrodes and a fourth of the plurality of electrical traces is operatively connected to a second of the plurality of ground electrodes, wherein the plurality of electrical traces are conformally disposed on the complex curved surface of the acoustic backing structure using additive fabrication; and
a plurality of ports connected to the acoustic backing structure, wherein each of the plurality of ports is connected to one of the plurality of electrical traces, wherein the acoustic backing structure is tapered so that it is wider at the curved surface than at the plurality of ports in a direction perpendicular to the plurality of planar surfaces.

2. The ultrasound transducer of claim 1, wherein a portion of the acoustic backing structure is chamfered to provide electrical isolation between the plurality of ground electrodes and the plurality of signal traces.

3. The ultrasound transducer of claim 1, further comprising an electrically insulating material disposed on at least a portion of the plurality of signal traces to electrically isolate the plurality of signal traces from the plurality of ground electrodes.

4. The ultrasound transducer of claim 1, wherein the plurality of signal electrodes and the plurality of ground electrodes form an interdigitated structure.

5. The ultrasound transducer of claim 1, further comprising an interposer flex circuit coupled to the transducer array.

6. The ultrasound transducer of claim 5, wherein a width of the interposer flex circuit is greater than a width of the acoustic backing structure.

7. The ultrasound transducer of claim 1, comprising one or more acoustic matching layers disposed on the first side of the transducer array.

8. An ultrasound transducer, comprising:
a transducer array having a first side and a second side and comprising a plurality of transducer elements;
a plurality of ground electrodes disposed on the first side of the transducer array;
a plurality of signal electrodes disposed on the second side of the transducer array;
an acoustic backing structure operatively coupled to the plurality of transducer elements of the transducer array, wherein the acoustic backing structure includes a complex curved surface; and
a plurality of electrical traces routed on the complex curved surface of the acoustic backing structure, wherein the plurality of electrical traces comprises a plurality of signal traces and a plurality of ground traces, wherein one or more signal traces of the plurality of signal traces have a varying thickness, wherein a first of the plurality of signal traces is operatively connected to a first of the plurality of signal electrodes and a second of the plurality of signal traces is operatively connected to a second of the plurality of the signal electrodes, wherein a first of the plurality of ground traces is operatively connected to a first of the plurality of ground electrodes and a second of the plurality of ground traces is operatively connected to a second of the plurality of ground electrodes, wherein the plurality of electrical traces are conformally disposed on the complex curved surface of the acoustic backing structure using additive fabrication.

9. The ultrasound transducer of claim 8, wherein a portion of the acoustic backing structure is chamfered to provide electrical isolation between the plurality of ground electrodes and the plurality of signal traces.

10. The ultrasound transducer of claim 8, further comprising an electrically insulating material disposed on at least a portion of the plurality of signal traces to electrically isolate the plurality of signal traces from the plurality of ground electrodes.

11. The ultrasound transducer of claim 8, wherein the plurality of signal electrodes and the plurality of ground electrodes form an interdigitated structure.

12. The ultrasound transducer of claim 8, further comprising an interposer flex circuit coupled to the transducer array.

13. The ultrasound transducer of claim 12, wherein a width of the interposer flex circuit is greater than a width of the acoustic backing structure.

14. The ultrasound transducer of claim 8, comprising one or more acoustic matching layers disposed on the first side of the transducer array.

* * * * *